US007323548B2

(12) United States Patent
Wallach et al.

(10) Patent No.: US 7,323,548 B2
(45) Date of Patent: Jan. 29, 2008

(54) MODULATORS OF THE FUNCTION OF FAS/APO1 RECEPTORS

(75) Inventors: David Wallach, Rehovot (IL); Mark Boldin, Moscow (RU); Eugene Varfolomeev, Rehovot (IL); Igor Mett, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 74 days.

(21) Appl. No.: 10/923,031

(22) Filed: Aug. 23, 2004

(65) Prior Publication Data

US 2005/0013816 A1 Jan. 20, 2005

Related U.S. Application Data

(60) Division of application No. 09/933,814, filed on Aug. 22, 2001, now Pat. No. 6,808,891, and a division of application No. 09/824,134, filed on Apr. 3, 2001, said application No. 09/933,814 and a division of application No. 08/860,082, filed on Aug. 19, 1997, now Pat. No. 7,108,999, is a division of application No. 08/860,082, filed on Aug. 19, 1997, said application No. 09/824,134 is a continuation of application No. 08/860,082, filed as application No. PCT/US95/16542 on Dec. 14, 1995.

(30) Foreign Application Priority Data

Dec. 15, 1994 (IL) ........................... 112002
Feb. 19, 1995 (IL) ........................... 112692
Jul. 16, 1995 (IL) ........................... 114615

(51) Int. Cl.
*C12P 21/08* (2006.01)
*C07K 16/00* (2006.01)
*A61K 39/395* (2006.01)

(52) U.S. Cl. ............... 530/387.1; 530/388.1; 530/389.1; 424/130.1

(58) Field of Classification Search ............. 530/387.1
See application file for complete search history.

(56) References Cited

U.S. PATENT DOCUMENTS 4,889,806 A 12/1989 Olson et al.

FOREIGN PATENT DOCUMENTS

WO  WO 96/12735 A1   5/1996
WO  WO 96/30404 A1  10/1996
WO  WO 96/31603 A2  10/1996
WO  WO 96/36730 A1  11/1996

OTHER PUBLICATIONS

Komada et al (Blood, 86(10): 3848-3860).*
Gura (Science, 1997, 278:1041-1042.).*

Ahn et al, "The structural and functional diversity of dystrophin." *Nature Genetics.* 3(4):283-91 (1993).
Baker et al, "Transducers of life and death: TNF receptor superfamily and associated proteins", *Oncogene* 12(1):1-9 91996.
Blau et al, "Gene Therapy—A Novel Form of Drug Delivery" *New Engl J Med* 2:333(18):1204-7 (1995).
Boldin et al, "Genbank Sequence Database (Accession X84709) and MPSRCH search report." us-09-824-134-1.rge (1995).
Boldin et al, "A novel protein that interacts with the death domain of Fas/APO1 contains a sequence motif related to the death domain", *J Biol Chem* 270(14):7795-7798 (1995).
Boldin et al, "Involvement of MACH, a Novel MORT1/FADD-Interacting Protease, in Fas/APO-1—and TNF Receptor-Induced Cell Death", *Cell* 85(6):803-815 (1996).
Branch, "A Good Antisense Molecule is Hard to Find." *Trends Biochem Sci.* 23(2):45-50 (1998).
Burgess et al, "Actvities of Heparin-binding (Acidiic Fibroblast) Growth Factor-1 from Its Receptor-binding Activities by Site-directed Mutagenesis of a Single Lysine Residue." *Journal of Cell Biology* 11:2129-2138 (1990).
Cawthon et al, "cDNA Sequence and Genomic Structure of *EVI2B*, a Gene Lying within an Intron of the Neurofibromatosis Type 1 Gene." *Genomics* 9(3):446-60, 1991.
Chinnaiyan et al, "FADD, a novel death domain-containing protein, interacts with the death domain of Fas and initiated apoptosis", *Cell* 81:505-512 (1995).
Clement et al, "Fas and Tumor Necrosis Factor Receptor Mediated Cell Death: Similarities and Distinctions", *J Exp Med* 180:557-567 (1994).
Crystal, "Transfer of Genes to Humans: Early Lessons and Obstacles to Success." *Science*, 270: 404-410 (1995).
Curti, "Physical barriers to drug delivery in tumors." *Cri Rev in Oncology/hematology.* 14:29-39 (1993).
Deonarain, "Ligand-targeted receptor-mediated vectors for gene deliver." *Expert Opin Ther Pat.* 8:53-69 (1998).
Freshney, *Culture of Animal Cells, A Manual of Basic Technique*, Alan R. Liss, Inc., New York: p. 4 (1983).
Gillies et al, "Antigen binding and biological activities of engineered mutant chimeric antibodies with human tumor specificities." *Human Antibodies and Hybridomas.* 1(1):47-54 (1990).
Gura, "Systems for Identifying New Drugs Are Often Faulty." *Science* 278:1041-1042 (1997).
Harris et al, "Polycystic Kidney Disease 1: Identification and Analysis of the Primary Defect." *The Am Society of Nephrology* 6:1125-33 (1995).
Hartwell et al, "Integrating Genetic Approaches into the Discovery of Anticancer Drugs." *Science* 278:1064-1068 (1997).
Jain, "Barriers to Drug Delivery in Solid Tumors." *Sci Am*, 271:58-65 (1994).
Lazar et al, "Transforming Growth Factor α: Mutation of Aspartic Acid 47 and Leucine 48 Results in Different Biological Activities." 8:1247-1252 (1988).

(Continued)

*Primary Examiner*—Misook Yu
*Assistant Examiner*—Sean E Aeder
(74) *Attorney, Agent, or Firm*—Browdy and Neimark, PLLC

(57) ABSTRACT

Proteins capable of modulating the function of FAS/APO1 are provided. The proteins may be prepared by culturing a host cell transformed with a vector containing the DNA encoding such a protein under suitable conditions and isolating the protein.

9 Claims, 7 Drawing Sheets

OTHER PUBLICATIONS

Marshall, "Gene Therapy's Growing Pains", *Science* 25:269(5227): 1050-5 (1995).

Miller, "Targeted vectors for gene therapy." *FASEB J.* 9:190-199 (1995).

Nagata et al, "Fas and Fas ligand: A death factor and its receptor", *Advances in Immunology* 57:129-144 (1994).

Rudert et al, *Biohysical and biophysical research communications*, 204(3):1102-1110 (1994).

Sambrook et al, *Molecular Cloning, A Laboratory Manual*. 2$^{nd}$ Ed., Cold Spring Harbor Press, Cold Spring Harbor, 16.3-16.4 (1989(.

Song et al, "Aggregation of the Intracellular Domain of the Type 1 Tumor Necrosis Receptor Defined by the Two-hybrid System", *J biol Chem* 269(36):22492-22495 (1994).

Tao et al, "Studies of Aglycosylated Chimeric Mouse-Human IgG: Role of Carbohydrate in the Structure and Effector Functions Mediated by the Human IgG Constant Region." *The Journal of Immunology*.

Verma, "Gene therapy- promises, problems and prospects." *Nature*. 389:239-242 (1997).

GenBank Accession No. Q13158: "FADD, a novel death domain-containing protein, interacts with the death domain of Fas and initiates apoptosis", Aug. 18, 2002.

GenBank Accession No. U24231: "Human Fas-assoiciating death domain-containing protein mRNA, complete cds", Aug. 18, 2002.

GenBank Accession No. Q15121: "Astrocytic phosphoprotein", Nov. 1, 1997.

GenBank Accession No. X86809: "*H. sapiens* mRNA for major astrocytic phosphoprotein PEA-15", Jul. 23, 1996.

GenBank Accession No. P16157: "Ankyrin 1 (Erythrocyte Ankyrin)", Apr. 1, 1990.

GenBank Accession No. P08138: "Low-affinity nerve growth factor receptor precursor (NGF receptor)", Aug. 1, 1988.

GenBank Accession No. P19438: "Tumor necrosis factor receptor 1 precursor (Tumor necrosis factor binding protein 1)", Feb. 1, 1991.

GenBank Accession No. NP_002459: "Myeloid differentiation primary response gene (88)", Mar. 19, 1999.

GenBank Accession No. P22366: "Myeloid differentiation primary response protein MYD88", Aug. 1, 1991.

GenBank Accession No. P35445: "FASL Receptor precursor (apoptosis-mediating surface antigen FAS) (APO-1 Antigen) (CD95 Antigen)", May 1, 1992.

GenBank Accession No. P53355: "Death-associated protein kinase 1 (DAP kinase 1)", Oct. 1, 1996.

MPSRCH search report, us-09-824-134-1.rge: 4-5 (2002).

MPSRCH search report, us-09-824-134-2.rpr:1 (2002).

\* cited by examiner

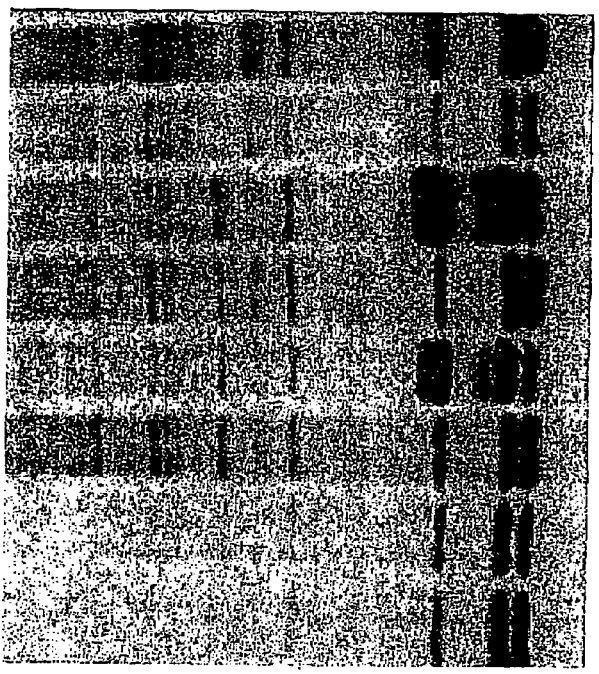
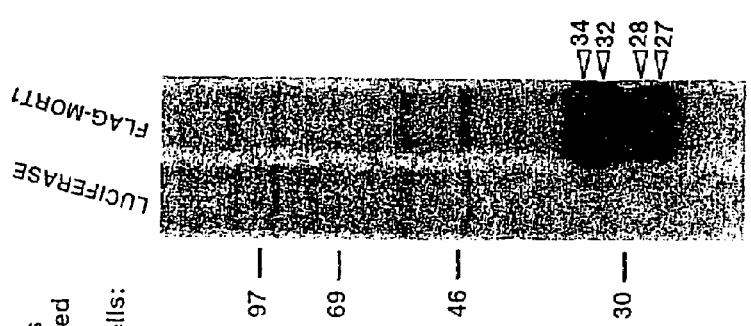
FIG. 1A Immunoprecip. with αFLAG Abs
FIG. 1B Binding to GST fusion proteins

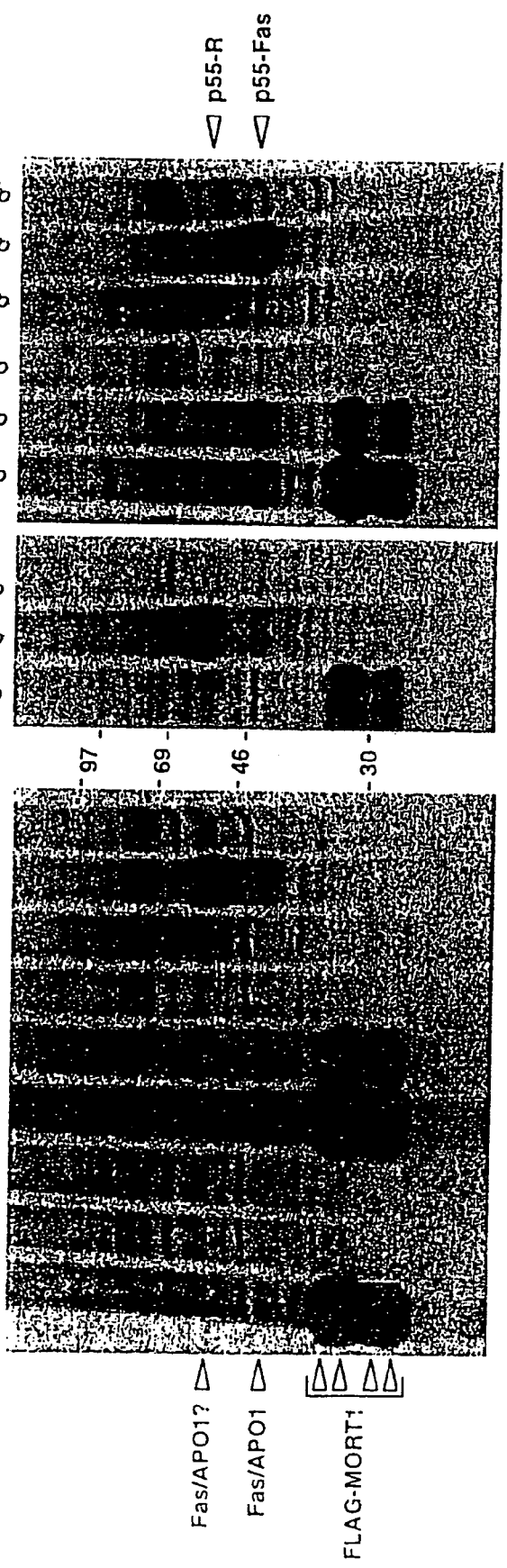

```
1/1                                         31/11
GTG AAT CAG GCA CCG GAG TGC AGG TTC GGG GGT GGA ATC CTT GGG CCG CTG GGC AAG CGG
 V   N   Q   A   P   E   C   R   F   G   G   G   I   L   G   P   L   G   K   R
61/21                                       91/31
CGA GAC CTG GCC AGG GCC AGC GAG CCG AGG ACA GAG GGC GCG CGG AGG GCC GGG CCG CAG
 R   D   L   A   R   A   S   E   P   R   T   E   G   A   R   R   A   G   P   Q
121/41                                      151/51
CCC CGG CCG CTT GCA GAC CCC GCC ATG GAC CCG TTC CTG GTG CTG CTG CAC TCG GTG TCG
 P   R   P   L   A   D   P   A   M   D   P   F   L   V   L   L   H   S   V   S
181/61                                      211/71
TCC AGC CTG TCG AGC AGC GAG CTG ACC GAG CTC AAG TTC CTA TGC CTC GGG CGC GTG GTC
 S   S   L   S   S   S   E   L   T   E   L   K   F   L   C   L   G   R   V   V
241/81                                      271/91
AAG CGC AAG CTG GAG CGC GTG CAG AGC GGC CTA GAC CTC TTC TCC ATG CTG CTG GAG CAG
 K   R   K   L   E   R   V   Q   S   G   L   D   L   F   S   M   L   L   E   Q
301/101                                     331/111
AAC GAC CTG GAG CCC GGG CAC ACC GAG CTC CTG CGC GAG CTG CTC GCC TCC CTG CGG CGC
 N   D   L   E   P   G   H   T   E   L   L   R   E   L   L   A   S   L   R   R
361/121                                     391/131
CAC GAC CTG CTG CGG CGC GTC GAC GAC TTC GAG GCG GGG GCG GCG GCC GGG GCC GCG CCT
 H   D   L   L   R   R   V   D   D   F   E   A   G   A   A   A   G   A   A   P
421/141                                     451/151
GGG GAA GAA GAC CTG TGT GCA GCA TTT AAC GTC ATA TGT GAT AAT GTG GGG AAA GAT TGG
 G   E   E   D   L   C   A   A   F   N   V   I   C   D   N   V   G   K   D   W
481/161                                     511/171
AGA AGG CTG GCT CGT CAG CTC AAA GTC TCA GAC ACC AAG ATC GAC AGC ATC GAG GAC AGA
 R   R   L   A   R   Q   L   K   V   S   D   T   K   I   D   S   I   E   D   R
541/181                                     571/191
TAC CCC CGC AAC CTG ACA GAG CGT GTG CGG GAG TCA CTG AGA ATC TGG AAG AAC ACA GAG
 Y   P   R   N   L   T   E   R   V   R   E   S   L   R   I   W   K   N   T   E
601/201                                     631/211
AAG GAG AAC GCA ACA GTG GCC CAC CTG GTG GGG GCT CTC AGG TCC TGC CAG ATG AAC CTG
 K   E   N   A   T   V   A   H   L   V   G   A   L   R   S   C   Q   M   N   L
661/221                                     691/231
GTG GCT GAC CTG GTA CAA GAG GTT CAG CAG GCC CGT GAC CTC CAG AAC AGG AGT GGG GCC
 V   A   D   L   V   Q   E   V   Q   Q   A   R   D   L   Q   N   R   S   G   A
721/241                                     751/251
ATG TCC CCG ATG TCA TGG AAC TCA GAC GCA TCT ACC TCC GAA GCG TCC TGA TGG GCC GCT
 M   S   P   M   S   W   N   S   D   A   S   T   S   E   A   S   *
781/261                                     811/271
GCT TTG CGC TGG TGG ACC ACA GGC ATC TAC ACA GCC TGG ACT TTG GTT CTC TCC AGG AAG
841/281                                     871/291
GTA GCC CAG CAC TGT GAA GAC CCA GCA GGA AGC CAG GCT GAG TGA GCC ACA GAC CAC CTG
901/301                                     931/311
CTT CTG AAC TCA AGC TGC GTT TAT TAA TGC CTC TCC CGC ACC AGG CCG GGC TTG GGC CCT
961/321                                     991/331
GCA CAG ATA TTT CCA TTT CTT CCT CAC TAT GAC ACT GAG CAA GAT CTT GTC TCC ACT AAA
1021/341                                    1051/351
TGA GCT CCT GCG GGA GTA GTT GGA AAG TTG GAA CCG TGT CCA GCA CAG AAG GAA TCT GTG
1081/361                                    1111/371
CAG ATG AGC AGT CAC ACT GTT ACT CCA CAG CGG AGG AGA CCA GCT CAG AGG CCC AGG AAT
1141/381                                    1171/391
CGG AGC GAA GCA GAG AGG TGG AGA ACT GGG ATT TGA ACC CCC GCC ATC CTT CAC CAG AGC
1201/401                                    1231/411
CCA TGC TCA ACC ACT GTG GCG TTC TGC TGC CCC TGC AGT TGG CAG AAA GGA TGT TTT TGT
1261/421                                    1291/431
CCC ATT TCC TTG GAG GCC ACC GGG ACA GAC CTG GAC ACT AGG GTC AGG CGG GGT GCT GTG
1321/441                                    1351/451
GTG GGG AGA GGC ATG GCT GGG GTG GGG GTG GGG AGA CCT GGT TGG CCG TGG TCC AGC TCT
1381/461                                    1411/471
TGG CCC CTG TGT GAG TTG AGT CTC CTC TCT GAG ACT GCT AAG TAG GGG CAG TGA TGG TTG
1441/481                                    1471/491
CCA GGA CGA ATT GAG ATA ATA TCT GTG AGG TGC TGA TGA GTG ATT GAC ACA CAG CAC TCT
1501/501                                    1531/511
CTA AAT CTT CCT TGT GAG GAT TAT GGG TCC TGC AAT TCT ACA GTT TCT TAC TGT TTT GTA
1561/521                                    1591/531
TCA AAA TCA CTA TCT TTC TGA TAA CAG AAT TGC CAA GGC AGC GGG ATC TCG TAT CTT TAA
1621/541                                    1651/551
AAA GCA GTC CTC TTA TTC CTA AGG TAA TCC TAT TAA AAC ACA GCT TTA CAA CTT CCA TAT
1681/561
TAC AAA AAA AAA AAA AAA AAA
```

FIG. 4

SEQUENCE LISTING

```
<160> NUMBER OF SEQ ID NOS: 2

<210> SEQ ID NO 1
<211> LENGTH: 1701
<212> TYPE: DNA
<213> ORGANISM: Homo sapiens
<220> FEATURE:
<221> NAME/KEY: CDS
<222> LOCATION: (1)..(768)

<400> SEQUENCE: 1 gtg aat cag gca ccg gag tgc agg ttc ggg ggt gga atc ctt ggg ccg        48
Val Asn Gln Ala Pro Glu Cys Arg Phe Gly Gly Gly Ile Leu Gly Pro
 1               5                  10                  15 ctg ggc aag cgg cga gac ctg gcc agg gcc agc gag ccg agg aca gag        96
Leu Gly Lys Arg Arg Asp Leu Ala Arg Ala Ser Glu Pro Arg Thr Glu
            20                  25                  30 ggc gcg cgg agg gcc ggg ccg cag ccc cgg ccg ctt gca gac ccc gcc       144
Gly Ala Arg Arg Ala Gly Pro Gln Pro Arg Pro Leu Ala Asp Pro Ala
        35                  40                  45 atg gac ccg ttc ctg gtg ctg ctg cac tcg gtg tcg tcc agc ctg tcg       192
Met Asp Pro Phe Leu Val Leu Leu His Ser Val Ser Ser Ser Leu Ser
    50                  55                  60 agc agc gag ctg acc gag ctc aag ttc cta tgc ctc ggg cgc gtg gtc       240
Ser Ser Glu Leu Thr Glu Leu Lys Phe Leu Cys Leu Gly Arg Val Val
65                  70                  75                  80 aag cgc aag ctg gag cgc gtg cag agc ggc cta gac ctc ttc tcc atg       288
Lys Arg Lys Leu Glu Arg Val Gln Ser Gly Leu Asp Leu Phe Ser Met
                85                  90                  95 ctg ctg gag cag aac gac ctg gag ccc ggg cac acc gag ctc ctg cgc       336
Leu Leu Glu Gln Asn Asp Leu Glu Pro Gly His Thr Glu Leu Leu Arg
            100                 105                 110 gag ctg ctc gcc tcc ctg cgg cgc cac gac ctg ctg cgg cgc gtc gac       384
Glu Leu Leu Ala Ser Leu Arg Arg His Asp Leu Leu Arg Arg Val Asp
        115                 120                 125 gac ttc gag gcg ggg gcg gcg gcc ggg gcc gcg cct ggg gaa gaa gac       432
Asp Phe Glu Ala Gly Ala Ala Ala Gly Ala Ala Pro Gly Glu Glu Asp
    130                 135                 140 ctg tgt gca gca ttt aac gtc ata tgt gat aat gtg ggg aaa gat tgg       480
Leu Cys Ala Ala Phe Asn Val Ile Cys Asp Asn Val Gly Lys Asp Trp
145                 150                 155                 160
```

-continued

| | | | | | | | | | | | | |
|---|---|---|---|---|---|---|---|---|---|---|---|---|
| aga | agg | ctg | gct | cgt | cag | ctc | aaa | gtc | tca | gac | acc | aag atc gac agc | 528 |
| Arg | Arg | Leu | Ala | Arg | Gln | Leu | Lys | Val | Ser | Asp | Thr | Lys Ile Asp Ser |
| | | | 165 | | | | | 170 | | | | 175 |

| atc | gag | gac | aga | tac | ccc | cgc | aac | ctg | aca | gag | cgt | gtg cgg gag tca | 576 |
|---|---|---|---|---|---|---|---|---|---|---|---|---|---|
| Ile | Glu | Asp | Arg | Tyr | Pro | Arg | Asn | Leu | Thr | Glu | Arg | Val Arg Glu Ser |
| | | | 180 | | | | | 185 | | | | 190 |

| ctg | aga | atc | tgg | aag | aac | aca | gag | aag | gag | aac | gca | aca gtg gcc cac | 624 |
|---|---|---|---|---|---|---|---|---|---|---|---|---|---|
| Leu | Arg | Ile | Trp | Lys | Asn | Thr | Glu | Lys | Glu | Asn | Ala | Thr Val Ala His |
| | | 195 | | | | | 200 | | | | | 205 |

| ctg | gtg | ggg | gct | ctc | agg | tcc | tgc | cag | atg | aac | ctg | gtg gct gac ctg | 672 |
|---|---|---|---|---|---|---|---|---|---|---|---|---|---|
| Leu | Val | Gly | Ala | Leu | Arg | Ser | Cys | Gln | Met | Asn | Leu | Val Ala Asp Leu |
| | | 210 | | | | | 215 | | | | | 220 |

| gta | caa | gag | gtt | cag | cag | gcc | cgt | gac | ctc | cag | aac | agg agt ggg gcc | 720 |
|---|---|---|---|---|---|---|---|---|---|---|---|---|---|
| Val | Gln | Glu | Val | Gln | Gln | Ala | Arg | Asp | Leu | Gln | Asn | Arg Ser Gly Ala |
| 225 | | | | 230 | | | | | 235 | | | 240 |

| atg | tcc | ccg | atg | tca | tgg | aac | tca | gac | gca | tct | acc | tcc gaa gcg tcc | 768 |
|---|---|---|---|---|---|---|---|---|---|---|---|---|---|
| Met | Ser | Pro | Met | Ser | Trp | Asn | Ser | Asp | Ala | Ser | Thr | Ser Glu Ala Ser |
| | | | | 245 | | | | | 250 | | | 255 |

| | |
|---|---|
| tgatgggccg ctgctttgcg ctggtggacc acaggcatct acacagcctg gactttggtt | 828 |
| ctctccagga aggtagccca gcactgtgaa gacccagcag gaagccaggc tgagtgagcc | 888 |
| acagaccacc tgcttctgaa ctcaagctgc gtttattaat gcctctcccg caccaggccg | 948 |
| ggcttgggcc ctgcacagat atttccattt cttcctcact atgacactga gcaagatctt | 1008 |
| gtctccacta aatgagctcc tgcgggagta gttggaaagt tggaaccgtg tccagcacag | 1068 |
| aaggaatctg tgcagatgag cagtcacact gttactccac agcggaggag accagctcag | 1128 |
| aggcccagga atcggagcga agcagagagg tggagaactg ggatttgaac ccccgccatc | 1188 |
| cttcaccaga gcccatgctc aaccactgtg gcgttctgct gcccctgcag ttggcagaaa | 1248 |
| ggatgttttt gtcccatttc cttggaggcc accgggacag acctggacac tagggtcagg | 1308 |
| cggggtgctg tggtggggag aggcatggct ggggtgcggg tggggagacc tggttggccg | 1368 |
| tggtccagct cttggcccct gtgtgagttg agtctcctct ctgagactgc taagtagggg | 1428 |
| cagtgatggt tgccaggacg aattgagata atatctgtga ggtgctgatg agtgattgac | 1488 |
| acacagcact ctctaaatct tccttgtgag gattatgggt cctgcaattc tacagtttct | 1548 |
| tactgtttg tatcaaaatc actatctttc tgataacaga attgccaagg cagcgggatc | 1608 |
| tcgtatcttt aaaaagcagt cctcttattc ctaaggtaat cctattaaaa cacagcttta | 1668 |
| caacttccat attacaaaaa aaaaaaaaaa aaa | 1701 |

<210> SEQ ID NO 2
<211> LENGTH: 256
<212> TYPE: PRT
<213> ORGANISM: Homo sapiens

<400> SEQUENCE: 2

Val Asn Gln Ala Pro Glu Cys Arg Phe Gly Gly Ile Leu Gly Pro
1               5                  10                 15

Leu Gly Lys Arg Arg Asp Leu Ala Arg Ala Ser Glu Pro Arg Thr Glu
            20                  25                  30

Gly Ala Arg Arg Ala Gly Pro Gln Pro Arg Pro Leu Ala Asp Pro Ala
        35                  40                  45

Met Asp Pro Phe Leu Val Leu His Ser Val Ser Ser Leu Ser
    50                  55                  60

Ser Ser Glu Leu Thr Glu Leu Lys Phe Leu Cys Leu Gly Arg Val Val
65                  70                  75                  80

```
Lys Arg Lys Leu Glu Arg Val Gln Ser Gly Leu Asp Leu Phe Ser Met
            85                  90                  95

Leu Leu Glu Gln Asn Asp Leu Glu Pro Gly His Thr Glu Leu Leu Arg
            100                 105                 110

Glu Leu Leu Ala Ser Leu Arg Arg His Asp Leu Leu Arg Arg Val Asp
        115                 120                 125

Asp Phe Glu Ala Gly Ala Ala Ala Gly Ala Ala Pro Gly Glu Glu Asp
        130                 135                 140

Leu Cys Ala Ala Phe Asn Val Ile Cys Asp Asn Val Gly Lys Asp Trp
145                 150                 155                 160

Arg Arg Leu Ala Arg Gln Leu Lys Val Ser Asp Thr Lys Ile Asp Ser
                165                 170                 175

Ile Glu Asp Arg Tyr Pro Arg Asn Leu Thr Glu Arg Val Arg Glu Ser
            180                 185                 190

Leu Arg Ile Trp Lys Asn Thr Glu Lys Glu Asn Ala Thr Val Ala His
            195                 200                 205

Leu Val Gly Ala Leu Arg Ser Cys Gln Met Asn Leu Val Ala Asp Leu
        210                 215                 220

Val Gln Glu Val Gln Gln Ala Arg Asp Leu Gln Asn Arg Ser Gly Ala
225                 230                 235                 240

Met Ser Pro Met Ser Trp Asn Ser Asp Ala Ser Thr Ser Glu Ala Ser
                245                 250                 255
```

MODULATORS OF THE FUNCTION OF FAS/APO1 RECEPTORS

FIELD OF THE INVENTION

The present invention is generally in the field of receptors belonging to the TNF/NGF superfamily of receptors and the control of their biological functions. The TNF/NGF superfamily of receptors includes receptors such as the p55 and p75 tumor necrosis factor receptors (TNF-Rs) and the FAS ligand receptor (also called FAS/APO1 or FAS-R and hereinafter will be called FAS-R) and others. More specifically, the present invention concerns a novel protein, herein designated MORT-1 (also called HF-1) which binds to the intracellular domain (IC) of the Fas-R, (this intracellular domain designated Fas-IC) and which novel protein is capable of modulating the function of the Fas-R. Further, MORT-I is also capable of self-association and can activate cell cytotoxicity on its own. The present invention also concerns the preparation and uses of MORT-1.

It should be noted that HF-1 (the original designation) and MORT-1 (the presently used designation) are both used throughout the specification and denote the same protein.

BACKGROUND OF THE INVENTION AND PRIOR ART

Tumor Necrosis Factor (TNF-α) and Lymphotoxin (TNF-β (hereinafter, TNF, refers to both TNF-α and TNF-β) are multifunctional pro-inflammatory cytokines formed mainly by mononuclear phagocytes, which have many effects on cells (Wallach, D. (1986) in: Interferon 7 (Ion Gresser, ed.), pp. 83-122, Academic Press, London; and Beutler and Cerami (1987)). Both TNF-α and TNF-β initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-α and TNF-β also have deleterious effects. There is evidence that over-production of TNF-α can play a major pathogenic role in several diseases. Thus, effects of TNF-α, primarily on the vasculature, are now known to be a major cause for symptoms of septic shock (Tracey et al., 1986). In some diseases, TNF may cause excessive loss of weight (cachexia) by suppressing activities of adipocytes and by causing anorexia, and TNF-α was thus called cachectin. It was also described as a mediator of the damage to tissues in rheumatic diseases (Beutler and Cerami, 1987) and as a major mediator of the damage observed in graft-versus-host reactions (Piques et al., 1987). In addition, TNF is known to be involved in the process of inflammation and in many other diseases.

Two distinct, independently expressed, receptors, the p55 and p75 TNF-As, which bind both TNF-α and TNF-β specifically, initiate and/or mediate the above noted biological effects of TNF. These two receptors have structurally dissimilar intracellular domains suggesting that they signal differently (See Hohmann et al., 1989; Engelmann et al., 1990; Brockhaus et al., 1990; Leotscher et al., 1990; Schall et al., 1990; Nophar et al., 1990; Smith et al., 1990; and Heller et al., 1990). However, the cellular mechanisms, for example, the various proteins and possibly other factors, which are involved in the intracellular signaling of the p55 an p75 TNF-Rs have yet to be elucidated (In PCT/US95/05854 and as set forth also herein below, there are described for the first time, new proteins capable of binding to the p75IC and p55IC). It is this intracellular signaling, which occurs usually after the binding of the ligand, i.e., TNF (α or β, to the receptor, that is responsible for the commencement of the cascade of reactions that ultimately result in the observed response of the cell to TNF.

As regards the above mentioned cytocidal effect of TNF, in most cells studied so far, this effect is triggered mainly by the p55 TNF-R. Antibodies against the extracellular domain (ligand binding domain) of the p55 TNF-R can themselves trigger the cytocidal effect (see EP 412486) which correlates with the effectivity of receptor cross-linking by the antibodies, believed to be the first step in the generation of the intracellular signaling process. Further, mutational studies (Brakebusch et al., 1992; Tartaglia et al., 1993) have shown that the biological function of the p55 TNF-R depends on the integrity of its intracellular domain, and accordingly it has been suggested that the initiation of intracellular signaling leading to the cytocidal effect of TNF occurs as a consequence of the association of two or more intracellular domains of the p55 TNF-R. Moreover, TNF (α and β) occurs as a homotrimer and as such has been suggested to induce intracellular signaling via the p55 TNF-R by way of its ability to bind to and to cross-link the receptor molecules, i.e., cause receptor aggregation. In PCT/US95/05854 and also hereinbelow there is described how the p55IC and p55DD can self-associate and induce, in a ligand-independent fashion, TNF-associated effects in cells.

Another member of the TNF/NGF superfamily of receptors is the FAS receptor (FAS-R) which has also been called the Fas antigen, a cell-surface protein expressed in various tissues and sharing homology with a number of cell-surface receptors including TNF-R and NGF-R. The FAS-R mediates cell death in the form of apoptosis (Itoh et al., 1991), and appears to serve as a negative selector of autoreactive T cells, i.e., during maturation of T cells, FAS-R mediates the apoptotic death of T cells recognizing self-antigens. It has also been found that mutations in the FAS-R gene (lpr) cause a lymphoproliferation disorder in mice that resembles the human autoimmune disease systemic lupus erythematosus (SLE) (Watanabe-Fukunaga et al., 1992). The ligand for the FAS-R appears to be a cell-surface associated molecule carried by, amongst others, killer T cells (or cytotoxic T lymphocytes—CTLs), and hence when such CTLs contact cells carrying FAS-R, they are capable of inducing apoptotic cell death of the FAS-R-carrying cells. Further, a monoclonal antibody has been prepared that is specific for FAS-R, this monoclonal antibody being capable of inducing apoptotic cell death in cells carrying FAS-R, including mouse cells transformed by cDNA encoding human FAS-R (Itoh et al., 1991).

It has also been found that various other normal cells, besides T lymphocytes, express the FAS-R on their surface and can be killed by the triggering of this receptor. Uncontrolled induction of such a killing process is suspected to contribute to tissue damage in certain diseases, for example, the destruction of liver cells in acute hepatitis. Accordingly, finding ways to restrain the cytotoxic activity of FAS-R may have therapeutic potential.

Conversely, since it has also been found that certain malignant cells and HIV-infected cells carry the FAS-R on their surface, antibodies against FAS-R, or the FAS-R ligand, may be used to trigger the FAS-R mediated cytotoxic effects in these and thereby provide a means for combating such malignant cells or HIV-infected cells (see Itoh et al., 1991). Finding yet other ways for enhancing the cytotoxic activity of FAS-R may therefore also have therapeutic potential.

It has been a long felt need to provide a way for modulating the cellular response to TNF (α or β) and FAS-R ligand, for example, in pathological situations as mentioned above, where TNF or FAS-R ligand is over-expressed it is desirable to inhibit the TNF- or FAS-R ligand-induced cytocidal effects, while in other situations, e.g., wound healing applications, it is desirable to enhance the TNF effect, or in the case of FAS-R, in tumor cells or HIV-infected cells it is desirable to enhance the FAS-R mediated effect.

A number of approaches have been made by the present inventors (see for example, European Application Nos. EP 186833, EP 308378, EP 398327 and EP 412486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-Rs. Further, on the basis that TNF-binding to its receptors is required for the TNF-induced cellular effects, approaches by the present inventors (see for example IL 101769 and its corresponding EP 568925) have been made to modulate the TNF effect by modulating the activity of the TNF-Rs. Briefly, EP 568925 (IL 101769) relates to a method of modulating signal transduction and/or cleavage in TNF-Rs whereby peptides or other molecules may interact either with the receptor itself or with effector proteins interacting with the receptor, thus modulating the normal functioning of the TNF-Rs. In EP 568925 there is described the construction and characterization of various mutant p55 TNF-Rs, having mutations in the extracellular, transmembranal, and intracellular domains of the p55 TNF-R. In this way regions within the above domains of the p55 TNF-R were identified as being essential to the functioning of the receptor, i.e., the binding of the ligand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of the TNF-R, which proteins, peptides and other factors may be involved in regulating or modulating the activity of the TNF-R. A number of approaches for isolating and cloning the DNA sequences encoding such proteins and peptides; for constructing expression vectors for the production of these proteins and peptides; and for the preparation of antibodies or fragments thereof which interact with the TNF-R or with the above proteins and peptides that bind various regions of the TNF-R, are also set forth in EP 568925. However, EP 568925 does not specify the actual proteins and peptides which bind to the intracellular domains of the TNF-Rs (e.g., p55 TNF-R), nor does it describe the yeast two-hybrid approach to isolate and identify such proteins or peptides which bind to the intracellular domains of TNF-Rs. Similarly, heretofore there has been no disclosure of proteins or peptides capable of binding the intracellular domain of FAS-R.

Thus, when it is desired to inhibit the effect of TNF, or the FAS-R ligand, it would be desirable to decrease the amount or the activity of TNF-Rs or FAS-R at the cell surface, while an increase in the amount or the activity of TNF-Rs or FAS-R would be desired when an enhanced TNF or FAS-R ligand effect is sought. To this end the promoters of both the p55 TNF-R and the p75 TNF-R have been sequenced, analyzed and a number of key sequence motifs have been found that are specific to various transcription regulating factors, and as such the expression of these TNF-Rs can be controlled at their promoter level, i.e., inhibition of transcription from the promoters for a decrease in the number of receptors, and an enhancement of transcription from the promoters for an increase in the number of receptors (see IL 104355 and IL 109633). Corresponding studies concerning the control of FAS-R at the level of the promoter of the FAS-R gene have yet to be reported.

Further, it should also be mentioned that, while it is known that the tumor necrosis factor (TNF) receptors, and the structurally-related receptor FAS-R, trigger in cells, upon stimulation by leukocyte-produced ligands, destructive activities that lead to their own demise, the mechanisms of this triggering are still little understood. Mutational studies indicate that in FAS-R and the p55 TNF receptor (p55-R) signaling for cytotoxicity involve distinct regions within their intracellular domains (Brakebusch et al., 1992; Tartaglia et al., 1993; Itoh and Nagata, 1993). These regions (the 'death domains') have sequence similarity. The 'death domains' of both FAS-R and p55-R tend to self-associate. Their self-association apparently promotes that receptor aggregation which is necessary for initiation of signaling (see PCT/US95/05854, as well as Song et al., 1994; Wallach et al., 1994; Boldin et al., 1995) and at high levels of receptor expression can result in triggering of ligand-independent signaling (PCT/US95/05854 and Boldin et al., 1995).

Thus, prior to PCT/US95/05854 and the present invention, there have not been provided proteins which may regulate the effect of ligands belonging to the TNF/NGF superfamily, such as the TNF or FAS-R ligand effect on cells, by mediation of the intracellular signaling process, which signaling is probably governed to a large extent by the intracellular domains (ICs) of the receptors belonging to the TNF/NGF superfamily of receptors, such as those of the TNF-Rs, i.e., the p55 and p75 TNF-R intracellular domains (p55IC and p75IC, respectively), as well as the FAS-IC.

Accordingly, it is one aim of the invention to provide proteins, being MORT-1, analogs, fragments or derivatives thereof, which are capable of binding to the intracellular domain of the FAS-R, which proteins are presently believed to be involved in the intracellular signaling process initiated by the binding of FAS ligand to its receptor. The MORT-1 protein, analogs, fragments and derivatives thereof of the present invention are distinct from the FAS-IC-binding proteins described in the earlier mentioned applications Another aim of the invention is to provide antagonists (e.g., antibodies) to these FAS-IC binding molecules, being the MORT-1 protein, analogs fragments and derivatives, which may be used to inhibit the signaling process, when desired, when such FAS-IC-binding proteins are positive signal effectors (i.e., induce signaling), or to enhance the signaling process, when desired, when such FAS-IC-binding proteins are negative signal effectors (i.e., inhibit signaling).

Yet another aim of the invention is to use such MORT-1 protein, analogs, fragments and derivatives, to isolate and characterize additional proteins or factors, which may, for example, be involved further downstream in the signaling process, and/or to isolate and identify other receptors further upstream in the signaling process to which these MORT-1 protein, analogs, fragments and derivatives bind (e.g., other FAS-Rs or related receptors), and hence, in whose function they are also involved. Moreover, it is an aim of the present invention to use the above-mentioned MORT-1 protein, analogs, fragments and derivatives as antigens for the preparation of polyclonal and/or monoclonal antibodies thereto. The antibodies, in turn, may be used, for example, for the purification of the new MORT-1 protein from different sources, such as cell extracts or transformed cell lines.

Furthermore, these antibodies may be used for diagnostic purposes, e.g., for identifying disorders related to abnormal functioning of cellular effects mediated by the FAS-R receptor.

A further aim of the invention is to provide pharmaceutical compositions comprising the above MORT-1 protein, analogs, fragments or derivatives, as well as pharmaceutical compositions comprising the above noted antibodies or other antagonists.

SUMMARY OF THE INVENTION

In accordance with the present invention, we have found a novel protein which is capable of binding to the intracellular domain of the FAS-R. This FAS-IC-binding protein may act as a mediator or modulator of the FAS-R ligand effect on cells by way of mediating or modulating the intracellular signaling process which usually occurs following the binding of the FAS-R ligand at the cell surface.

This novel protein has been designated HF1, or MORT-1 (for 'Mediator of Receptor Toxicity'), and in addition to its FAS-IC-binding specificity has other characteristics (see Example 1), for example, it has a region homologous to the 'death domain' (DD) regions of the p55-TNF-R and FAS-R (p55-DD and FAS-DD), and thereby is also capable of self-association. MORT-1 is also capable of activating cell cytotoxicity on its own, an activity possibly related to its self-association capability. It has now also been found that co-expression of the region in MORT-1 (HF1) that contains the 'death domain' homology sequence (MORT-DD, present in the C-terminal part of MORT-1) strongly interferes with FAS-induced cell death, as would be expected from its ability to bind to the 'death domain' of the FAS-IC. Further, in the same experimental conditions it was found that co-expression of the part of MORT-1 that does not contain the MORT-DD region (the N-terminal part of MORT-1, amino acids 1-117, 'MORT-1 head') resulted in no interference of the FAS-induced cell death and, if at all, a somewhat enhanced FAS-induced cell cytotoxicity.

Accordingly, the present invention provides a DNA sequence encoding a herein designated MORT-1 protein, analogs, or fragments thereof, all of which are capable of binding to or interacting with the intracellular domain of the FAS-ligand receptor (FAS-IC).

In particular, the present invention provides a DNA sequence selected from the group consisting of:

(a) a cDNA sequence derived from the coding region of a native MORT-1 protein;

(b) DNA sequences capable of hybridization to a cDNA of (a) under moderately stringent conditions and which encode a biologically active FAS-R intracellular domain-binding protein; and (c) DNA sequences which are degenerate as a result of the genetic code to the DNA sequences defined in (a) and (b) and which encode a biologically active FAS-R intracellular domain-binding protein.

A specific embodiment of the above DNA sequence of the invention is a DNA sequence encoding the protein MORT-1 comprising the sequence depicted in FIG. 4.

The present invention also provides a MORT-1 protein, analogs, fragments or derivatives thereof encoded by any of the above sequences of the invention, said proteins, analogs, fragments and derivatives being capable of binding to or interacting with the intracellular domain of the FAS-R.

A specific embodiment of the above protein of the invention is the MORT-1 protein having the deduced amino acid sequence depicted in FIG. 4.

Also provided by the present invention are vectors encoding the above MORT-1 protein, analogs, fragments or derivatives of the invention, which contain the above DNA sequence of the invention, these vectors being capable of being expressed in suitable eukaryotic or prokaryotic host cells; transformed eukaryotic or prokaryotic host cells containing such vectors; and a method for producing the MORT-1 protein, analogs, conditions suitable for the expression of said protein, analogs, fragments or derivatives, effecting post-translational modifications of said protein as necessary for obtention of said protein and extracting said expressed protein, analogs, fragments or derivatives from the culture medium of said transformed cells or from cell extracts of said transformed cells.

In another aspect, the present invention also provides antibodies or active derivatives or fragments thereof specific to the MORT-1 protein, analogs, fragments and derivatives thereof, of the invention.

By yet another aspect of the invention, there are provided various uses of the above DNA sequences or the proteins which they encode, according to the invention, which uses include amongst others:

(i) a method for the modulation of the FAS-R ligand effect on cells carrying a FAS-R, comprising treating said cells with one or more MORT-1 protein, analogs, fragments or derivatives, according to the invention, all of which being capable of binding to the intracellular domain and modulating the activity of said FAS-R, wherein said treating of the cells comprises introducing into said cells said one or more MORT-1 protein, analogs, fragments or derivatives in a form suitable for intracellular administration or introducing into said cells, a DNA sequence encoding said one or more proteins, analogs, fragments or derivatives in the form of a suitable expression vector carrying said sequence, said vector being capable of effecting the insertion of said sequence into said cells in the way that said sequence is expressed in said cells;

(ii) a method for modulating the FAS-R ligand effect on cells comprising treating said cells with MORT-1, analogs, fragments or derivatives thereof, all being capable of binding to the intracellular domain and modifying the activity of FAS-R wherein said treating of cells comprises introducing into said cells said MORT-1, analogs, fragments or derivatives in a form suitable for intracellular introduction thereof, or introducing into said cells a DNA sequence encoding said MORT-1, analogs, fragments or derivatives in the form of a suitable vector carrying said sequence, said vector being capable of effecting the insertion of said sequence into said cells in a way that said sequence is expressed in said cells;

(iii) a method as in (ii) above wherein said treating of said cells is by transfection of said cells with a recombinant animal virus vector comprising the steps of:

(a) constructing a recombinant animal virus vector carrying a sequence encoding a viral surface protein (ligand) that is capable of binding to a specific cell surface receptor on the surface of a FAS-R-carrying cell and a second sequence encoding a protein selected from the MORT-1 protein, analogs, fragments and derivatives of the invention, that when expressed in said cells is capable of modulating the activity of said FAS-R; and (b) infecting said cells with said vector of (a).

(iv) a method for modulating the FAS-R ligand effect on cells carrying a FAS-R comprising treating said cells with antibodies or active derivatives or fragments thereof according to the invention, said treating being by application of a suitable composition containing said antibodies, active fragments or derivatives thereof to said cells, wherein when the MORT-1 proteins or portions thereof of said cells are exposed on the extracellular surface, said composition is formulated for extracellular application, and when said MORT-1 proteins are intracellular said composition is formulated for intracellular application;

(v) a method for modulating the FAS-R ligand effect on cells carrying a FAS-R comprising treating said cells with an oligonucleotide sequence encoding an antisense sequence of at least part of the MORT-I sequence of the invention, said oligonucleotide sequence being capable of blocking the expression of the MORT-1 protein;

(vi) a method as in (v) above wherein said treating of cells is by transfection of said cells with a recombinant animal virus vector comprising the steps of:
  (a) constructing a recombinant animal virus vector carrying a sequence encoding a viral surface protein (ligand) that is capable of binding to a specific cell surface receptor on the surface of a FAS-R-carrying cell and a second sequence which is an oligonucleotide sequence encoding an antisense sequence of at least part of the MORT-1 sequence according to the invention, said oligonucleotide sequence being capable of blocking the expression of the MORT-1 protein when introduced into said cells by said virus; and
  (b) infecting said cells with said vector of (a)

(vii) a method for treating tumor cells or HIV-infected cells, or other diseased cells, comprising:
  (a) constructing a recombinant animal virus vector carrying a sequence encoding a viral surface protein that is capable of binding to a tumor cell surface receptor or HIV-infected cell surface receptor or a receptor carried by other diseased cells and a sequence encoding a protein selected from the MORT-1 protein, analogs, fragments and derivatives of the invention, that when expressed in said tumor, HIV-infected cell, or other diseased cell is capable of killing said cell; and
  (b) infecting said tumor or HIV-infected cells or other diseased cells with said vector of (a).

(viii) a method for modulating the FAS-R ligand effect on cells comprising applying the ribozyme procedure in which a vector encoding a ribozyme sequence capable of interacting with a cellular mRNA sequence encoding a MORT-1 protein of the invention is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said MORT-1 protein in said cells;

(ix) a method selected from any of the above methods wherein said MORT-1 protein or said MORT-1 encoding sequence comprises at least that part of the MORT-1 protein which binds specifically to the FAS-IC, or at least that part of the MORT-1 encoding sequence that encodes that part of the MORT-1 protein which binds specifically to the FAS-IC;

(x) a method for isolating and identifying a protein capable of binding to the intracellular domain of FAS-R comprising applying the procedure of non-stringent southern hybridization followed by PCR cloning, in which a sequence or parts thereof according to the invention is used as a probe to bind sequences from a cDNA or genomic DNA library, having at least partial homology thereto, said bound sequences then amplified and cloned by the PCR procedure to yield clones encoding proteins having at least partial homology to said sequences according to the invention.

The present invention also provides a pharmaceutical composition for the modulation of the FAS ligand-effect on cells comprising, as active ingredient, any one of the following: (i) a MORT-1 protein according to the invention, its biologically active fragments, analogs, derivatives or mixtures thereof; (ii) a recombinant animal virus vector encoding a protein capable of binding a cell surface receptor and encoding a MORT-1 protein or its biologically active fragments or analogs according to the invention; and (iii) an oligonucleotide sequence encoding an antisense sequence of the MORT-1 sequence of the invention, wherein said oligonucleotide sequence may be the second sequence of the recombinant animal virus vector of (ii) above.

It should be mentioned that MORT-1 has a distinct region which binds to the FAS-IC and another distinct region which is involved in self-association of MORT-1, and accordingly, these distinct regions or parts thereof may be used independently to identify other proteins, receptors, etc. which are capable of binding to MORT-1 or to FAS-R and which may be involved in the MORT-1- or FAS-R-related intracellular signaling processes. Further, MORT-1 may have other activities associated with either of the above distinct regions or other regions of MORT-1 or combinations thereof, for example, enzymatic activity, which may be related to the cell cytotoxic effects of MORT-1 on its own. Thus, MORT-1 may also be used to specifically identify other proteins, peptides, etc. which may be involved in such additional activities associated with MORT-1.

Other aspects and embodiments of the present invention are also provided as arising from the following detailed description of the invention.

It should be noted that, where used throughout, the following terms: "Modulation of the FAS-ligand effect on cells"; and "Modulation of the MORT-1 effect on cells" are understood to encompass in vitro as well as in vivo treatment.

BRIEF DESCRIPTION OF THE DRAWINGS

FIGS. 1A and B are reproductions of autoradiograms of SDS-PAGE gels (10% acrylamide) showing the interaction between HF1 (MORT-1) and FAS-IC in vitro. FIG. 1A shows a control autoradiogram of an immunoprecipitate of the proteins (from extracts of HeLa cells transfected with the FLAG-HF1 (FLAG-MORT1) fusion protein or with the luciferase cDNA (control), the immunoprecipitation being performed with anti-FLAG antibody; and FIG. 1B shows an autoradiogram of a representative gel performed to evaluate the in vitro interaction between HF1 and FAS-IC by way of assessing, autoradiographically, the binding of [$^{35}$S]-methionine-metabolically labeled HF1 produced in transfected HeLa cells as a fusion protein with the FLAG octapeptide (FLAG-MORT1) to GST, human and mouse GST-FAS-IC fusion protein (GST-huFAS-IC, GST-mFAS-IC) and GST-FAS-IC fusion proteins in which the FAS-IC contained an Ile to Ala replacement mutation at position 225 (GST-mFAS-IC I225A). The [$^{35}$S]labeled proteins of the HeLa cells including the labeled FLAG-MORT1 fusion protein having been first extracted were subjected to interaction with the various GST and GST-FAS-IC proteins (bound to glutathione beads) and then to SDS-PAGE. As controls in all of the interaction experiments, extracts of HeLa cells transfected with luciferase were subjected to interactions with the GST and GST-FAS-IC fusion proteins and SDS-PAGE. FIGS. 1A and B are also described in Example 1.

FIGS. 2A, B and C are reproductions of autoradiograms of SDS-PAGE gels (10% acrylamide) on which were separated various immunoprecipitates from transfected HeLa cells and which show the in vivo interaction of HF1 (MORT1) with FAS-IC. The HeLa cells were transfected with DNA constructs encoding: HF1-FLAG (FLAG-MORT1) fusion protein alone, HF1-FLAG fusion protein and the human FAS-R (FLAG-MORT1+Fas/APO1) or human FAS-R alone (Fas/APO1) (FIG. 2A), or with HF1-FLAG fusion protein and the human p55-R (FLAG-MORT1+p55-R) (FIG. 2B); or with HF1-FLAG fusion protein and a chimeric fusion protein between human FAS-R and p55-R in which the extracellular domain of the FAS-R web replaced with the corresponding region of the p55-R (FLAG-MORT1+p55-FAS chimera) or the FAS-R-p55-R chimeric fusion protein alone (p55-Fas chimera) (FIG. 2C). In all cases the transfected cells were metabolically labeled with [$^{35}$S]cysteine (20 μCi/ml) and [$^{35}$S]methionine (40 μCi/ml), and were subjected to protein extraction. The protein extracts from the different transfected cells were then immunoprecipitated with various antibodies being anti-FLAG, anti-FAS, anti-p75-R and anti-p55-R antibodies (αFLAG, αFAS, αβ75-R and αβ55-R in FIGS. 2A-C) and subjected to SDS-PAGE. On the left side of FIG. 2A there is indicated the protein bands corresponding to FAS-R (Fas/APO1) and HF1-FLAG (FLAG-MORT1); between FIGS. 2A and B are shown the relative positions of standard molecular weight markers (in kDa), and on the right hand side of FIG. 2C the protein bands corresponding to p55R and the pS5-FAS chimera are indicated. FIGS. 2A-C are also described in Example 1.

FIGS. 4 depicts schematically the preliminary nucleotide (SEQ ID NO:1) and deduced amino acid sequence (SEQ ID NO:2) of HF1, as described in Example 1, in which the 'death domain' is underlined as is a possible translation start site, i.e., the underlined methionine residue at position 49 (bold, underlined M). The asterisk indicates the translation stop codon (nucleotides 769-771). At the beginning and in the middle of each line are provided two numerals depicting the relative positions of the nucleotides and amino acids of the sequence with respect to the start of the sequence (5' end), in which the first numeral denotes the nucleotide and the second numeral denoted the amino acid.

FIG. 5 shows the results of experiments to determine the C-terminal end of MORT-1, wherein FIG. 5 is a reproduction of an autoradiogram of an SDS-PAGE gel (10% acrylamide) on which were separated various MORT-1-FLAG fusion products expressed in HeLa cells-and metabolically labeled with $^{35}$S-cysteine and $^{35}$S-methionine followed by immunoprecipitation with either anti-FLAG monoclonal antibodies (M2) (lanes 2, 4 and 6) or as a control, anti-p75 TNF-R antibodies (49) (lanes 1, 3 and 5), as described in Example 1.

DETAILED DESCRIPTION OF THE INVENTION

Figure 3:
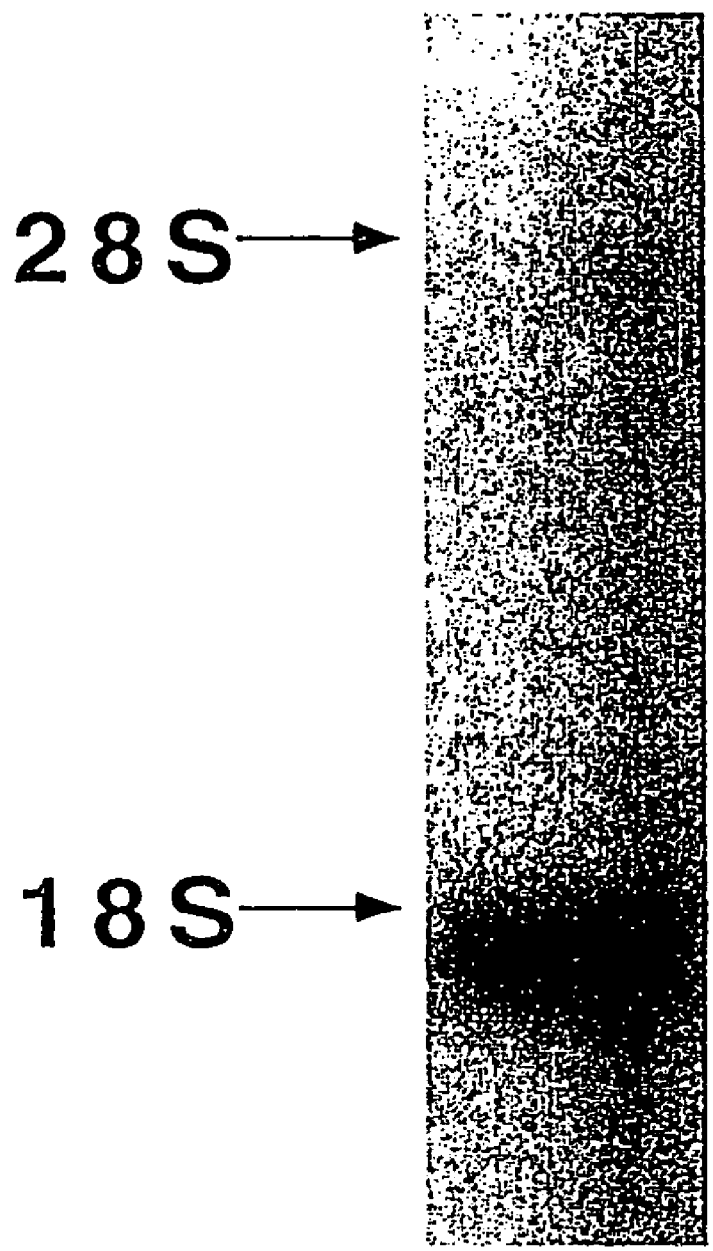
FIG. 3 shows a reproduction of a Northern blot in which poly A$^+$ RNA (0.3 μg) from HeLa cells transfected was probed with HF1 cDNA, as described in Example 1.

The present invention relates, in one aspect, to a novel protein MORT-1 (HF1) which is capable of binding to the intracellular domain of the FAS-R receptor, a member of the TNF/NGF superfamily and hence is considered as a mediator or modulator of FAS-R, having a role in, for example, the signaling process that is initiated by the binding of FAS ligand to FAS-R. The amino acid and DNA sequences of MORT-1 according to the invention also represent new sequences; they do not appear in the 'GENEBANK' or 'PROTEIN BANK' data banks of DNA or amino acid sequences.

Thus, the present invention concerns the DNA sequence encoding the MORT-1 protein and the MORT-1 protein encoded by the DNA sequences.

Moreover, the present invention also concerns the DNA sequences encoding biologically active analogs, fragments and derivatives of the MORT-1 protein, and the analogs, fragments and derivatives encoded thereby. The preparation of such analogs, fragments and derivatives is by standard procedure (see for example, Sambrook et al., 1989) in which in the DNA sequences encoding the MORT-1 protein, one or more codons may be deleted, added or substituted by another, to yield analogs having at least a one amino acid residue change with respect to the native protein. Acceptable analogs are those which retain at least the capability of binding to the intracellular domain of the FAS-R, or which can mediate any other binding or enzymatic activity, e.g., analogs which bind the FAS-IC but which do not signal, i.e., do not bind to a further downstream receptor, protein or other factor, or do not catalyze a signal-dependent reaction. In such a way analogs can be produced which have a so-called dominant-negative effect, namely, an analog which is defective either in binding to the FAS-IC, or in subsequent signaling following such binding. Such analogs can be used, for example, to inhibit the FAS-ligand-effect by competing with the natural FAS-IC-binding proteins. Likewise, so-called dominant-positive analogs may be produced which would serve to enhance the FAS ligand effect. These would have the same or better FAS-IC-binding properties and the same or better signaling properties of the natural FAS-IC-binding proteins. In an analogous fashion, biologically active fragments of MORT-1 may be prepared as noted above with respect to the analogs of MORT-1. Suitable fragments of MORT-1 are those which retain the FAS-IC binding capability or which can mediate any other binding or enzymatic activity as noted above. Accordingly, MORT-1 fragments can be prepared which have a dominant-negative or a dominant-positive effect as noted above with respect to the analogs. It should be noted that these fragments represent a special class of the analogs of the invention, namely, they are defined portions of MORT-1 derived from the full MORT-1 sequence, each such portion or fragment having any of the above-noted desired activities. Similarly, derivatives may be prepared by standard modifications of the side groups of one or more amino acid residues of the MORT-1 protein, its analogs or fragments, or by conjugation of the MORT-1 protein, its analogs or fragments, to another molecule, e.g., an antibody, enzyme, receptor, etc., as are well known in the art.

The new MORT-1 protein, its analogs, fragments and derivatives have a number of possible uses, for example:

(i) They may be used to mimic or enhance the function of FAS-R ligand, in situations where an enhanced FAS-R ligand effect is desired such as in anti-tumor, antiinflammatory or anti-HIV applications where the FAS-R ligand-induced cytotoxicity is desired. In this case the MORT-1 protein, its analogs, fragments or derivatives, which enhance the FAS-R ligand effect, i.e., cytotoxic effect, may be introduced to the cells by standard procedures known per se. For example, as the MORT-1 protein is intracellular and it should be introduced only into the cells where the FAS-R ligand effect is desired, a system for specific introduction of this protein into the cells is necessary. One way of doing this is by creating a recombinant animal virus, e.g., one derived from Vaccinia, to the DNA of which the following two genes will be introduced: the gene encoding a ligand that binds to cell surface proteins specifically expressed by the cells, e.g., ones such as the AIDS (HIV) virus gp120 protein which binds specifically to some cells (CD4 lymphocytes and related leukemias) or any other ligand that binds specifically to cells carrying a FAS-R, such that the recombinant virus vector will be capable of binding such FAS-R-carrying cells; and the gene encoding the MORT-1 protein. Thus, expression of the cell-surface-binding protein on the surface of the virus will target the virus specifically to the tumor cell or other FAS-R-carrying cell, following which the MORT-1 protein encoding sequence will be introduced into the cells via the virus, and once expressed in the cells will result in enhancement of the FAS-R ligand effect leading to the death of the tumor cells or other FAS-R-carrying cells it is desired to kill. Construction of such recombinant animal virus is by standard procedures (see for example, Sambrook et al., 1989). Another possibility is to introduce the sequences of the MORT-1 protein in the form of oligonucleotides which can be absorbed by the cells and expressed therein. A further possibility is by modifying the method described by Lin et al., in Journal of Biological Chemistry, Vol. 270, No. 24, pp. 14255-14258, 1995.

(ii) They may be used to inhibit the FAS-R ligand effect, e.g., in cases such as tissue damage in septic shock, graft-vs.-host rejection, or acute hepatitis, in which it is desired to block the FAS-R ligand induced FAS-R intracellular signaling. In this situation it is possible, for example, to introduce into the cells, by standard procedures, oligonucleotides having the anti-sense coding sequence for the MORT-1 protein, which would effectively block the translation of mRNAs encoding the MORT-1 protein and thereby block its expression and lead to the inhibition of the FAS-R ligand-effect. Such oligonucleotides may be introduced into the cells using the above recombinant virus approach, the second sequence carried by the virus being the oligonucleotide sequence.

Another possibility is to use antibodies specific for the MORT-1 protein to inhibit its intracellular signaling activity.

Yet another way of inhibiting the FAS-R ligand effect is by the recently developed ribozyme approach. Ribozymes are catalytic RNA molecules that specifically cleave RNAs. Ribozymes may be engineered to cleave target RNAs of choice, e.g., the mRNAs encoding the MORT-1 protein of the invention. Such ribozymes would have a sequence specific for the MORT-1 mRNA and would be capable of interacting therewith (complementary binding) followed by cleavage of the mRNA, resulting in a decrease (or complete loss) in the expression of the MORT-1 protein, the level of decreased expression being dependent upon the level of ribozyme expression in the target cell. To introduce ribozymes into the cells of choice (e.g., those carrying FAS-R) any suitable vector may be used, e.g., plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993; Shore et al., 1993; Joseph and Burke, 1993; Shimayarna et al., 1993; Cantor et al., 1993; Barinaga, 1993; Crisell et al., 1993 and Koizumi et al., 1993).

(iii) They may be used to isolate, identify and clone other proteins which are capable of binding to them, e.g., other proteins involved in the intracellular signaling process that are downstream of the TNF-R or FAS-R intracellular domain. For example, the MORT-1 protein, namely, the DNA sequence encoding it may be used in the yeast two-hybrid system (see Example 1, below) in which the sequence of the MORT-1 protein will be used as "bait" to isolate, clone and identify from cDNA or genomic DNA libraries other sequences ("preys") encoding proteins which can bind to the MORT-1 protein. In the same way, it may also be determined whether the MORT-1 protein of the present invention can bind to other cellular proteins, e.g., other receptors of the TNF/NGF superfamily of receptors.

(iv) The MORT-1 protein, its analogs, fragments or derivatives may also be used to isolate, identify and clone other proteins of the same class, i.e., those binding to FAS-R intracellular domain or to functionally related receptors, and involved in the intracellular signaling process. In this application the above noted yeast two-hybrid system may be used, or there may be used a recently developed system employing non-stringent southern hybridization followed by PCR cloning (Wilks et al., 1989). In the Wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the MORT-1 protein to identify and clone those of related FAS-R intracellular domain-binding proteins.

(v) Yet another approach to utilizing the MORT-1 protein, its analogs, fragments or derivatives of the invention is to use them in methods of affinity chromatography to isolate and identify other proteins or factors to which they are capable of binding, e.g., other receptors related to FAS-R or other proteins or factors involved in the intracellular signaling process. In this application, the MORT-1 protein, its analogs, fragments or derivatives of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the MORT-1 protein, its analogs, fragments or derivatives of the invention, can be eluted, isolated and characterized.

(vi) As noted above, the MORT-1 protein, its analogs, fragments or derivatives of the invention may also be used as immunogens (antigens) to produce specific antibodies thereto. These antibodies may also be used for the purposes of purification of the MORT-1 protein either from cell extracts or from transformed cell lines producing MORT-1, its analogs or fragments. Further, these antibodies may be used for diagnostic purposes for identifying disorders related to abnormal functioning of the FAS-R ligand system, e.g., overactive or underactive FAS-R ligand-induced cellular effects. Thus, should such disorders be related to a malfunctioning intracellular signaling system involving the MORT-1 protein, such antibodies would serve as an important diagnostic tool.

(vii) MORT-1 may also be used as an indirect modulator of a number of other proteins by virtue of its capability of binding to other intracellular proteins, (the so-called MORT-1 binding proteins, see below), which other intracellular proteins directly bind yet other intracellular proteins or an intracellular domain of a transmembrane protein. An example of such a protein or such an intracellular domain is the well-known p55 TNF receptor, the intracellular signaling of which is modulated by a number of proteins which bind directly to its intracellular domain (see copending IL 109632). In fact we have isolated such a MORT-1 binding protein (see below and Example 2) which binds to the intracellular domain of the p55 TNF receptor.

For the purposes of modulating these other intracellular proteins or the intracellular domains of transmembranal proteins, MORT-1 may be introduced into cells in a number of ways as mentioned hereinabove in (ii).

It should also be noted that the isolation, identification and characterization of the MORT-1 protein of the invention may be performed using any of the well known standard screening procedures. For example, one of these screening procedures, the yeast two-hybrid procedure as is set forth herein (Example 1), was used to identify the MORT-1 protein of the invention. Likewise as noted above and below, other procedures may be employed such as affinity chromatography, DNA hybridization procedures, etc. as are well known in the art, to isolate, identify and characterize the MORT-1 protein of the invention or to isolate, identify and characterize additional proteins, factors, receptors, etc. which are capable of binding to the MORT-1 protein of the invention.

Furthermore, it should also be noted that amongst the characteristics of MORT-1 is its ability to bind to the FAS-IC and also its ability to self-associate. MORT-1 is also capable of activating cell cytotoxicity on its own, an activity related to its self-association ability. It appears (see Example 1) that the part of MORT-1 which binds to the FAS-IC is distinct from the part of MORT-1 which is involved in its self-association. MORT-1 may also have other activities which may-be a function of the above noted distinct parts of the MORT-1 molecule or other parts of the molecule or combinations of any of these parts. These other activities may be enzymatic or related to binding other proteins (e.g., MORT-1-binding proteins or other receptors, factors, etc.). Thus, MORT-1 may be used in the above methods for modulation of FAS-R-ligand effects or its own MORT-1-mediated cellular effects, or it may be used in the modulation of other cellular signaling processes related to other receptors, factors, etc.

More specifically, by this aspect of the invention the MORT-1 encoding DNA molecule itself and mutations thereof (i.e., encoding analogs or active fractions of MORT-1) can be used for gene therapy (i.e., by the ways set forth in uses (i) and (ii) above) for modulating the activity of the FAS-R (or modulating or mediating the FAS ligand-effect on cells). Moreover, as MORT-1 also has a cytotoxic effect on cells, these MORT-1 or mutant MORT-1 encoding DNA molecules may also be used for gene therapy for modulating the MORT-1 effect in cells (also by way of the uses (i) and (ii) above). In these gene therapy applications, the MORT-1, analogs or derivatives may be used in three ways:

(a) the whole MORT-1 protein, its analogs, derivatives or active fragments which have both FAS-IC and MORT-1-binding ability (i.e., contain the two regions of MORT-1, one of which is involved in binding to FAS-IC and the other which is involved in the self-association of MORT-1) may be used to modulate FAS-R and MORT-1-associated effects;

(b) the part of MORT-1, and analogs, derivatives, and active fragments of this part which binds to the FAS-IC may be used for inducing a 'dominant negative' effect on FAS-IC, i.e., inhibition of FAS-R-mediated cellular effects, or may be used for inducing a 'gain of function' effect on FAS-IC, i.e., enhancement of the FAS-R-mediated cellular effects; and (c) the part of MORT-1 and analogs, derivatives and active fractions of this part, which binds specifically to MORT-1 may be used for induction of 'dominant negative' or 'gain of function' effects on MORT-1, i.e., either inhibition or enhancement of MORT-1-associated cellular effects.

As set forth in use (vi) above, the MORT-1 protein may be used to generate antibodies specific to MORT-1. These antibodies or fragments thereof may be used as set forth hereinbelow in detail, it being understood that in these applications the antibodies or fragments thereof are those specific for MORT-1.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, Nature 256:495-497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene publishing Assoc. and Wiley Interscience N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules different portions of which are derived from different animal species, such as those having the variable region derived from a murine mAb and a human immunoglobulin constant region. Chimeric antibodies are primarily used to reduce immunogenicity in application and to increase yields in production, for example, where murine mabs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:32733277 (1984); Morrison et al., Proc. Natl. Acad. Sci. USA 81:6851-6855 (1984); Boulianne et al., Nature 312:643-646 (1984); Cabilly et al., European Patent Application 125023 (published Nov. 14, 1984); Neuberger et al., Nature 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., J. Immunol. 137:1066-1074 (1986); Robinson et al., International Patent Application No. WO8702671 (published May 7, 1987); Liu et al., Proc. Natl. Acad Sci USA 84:3439-3443 (1987); Sun et al., Proc. Natl. Acad Sci USA 84:214-218 (1987); Better et al., Science 240:1041-1043 (1988); and Harlow and Lane, ANTIBODIES:A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the MORT-1 protein, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above MORT-1 protein, analogs, fragments or derivatives.

The anti-Id mAbs thus have their own idiotypic epitopes, or "idiotopes" structurally similar to the epitope being evaluated, such as GRB protein-α.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316-325 (1983)).

It will be appreciated that Fab and F(ab')$_2$ and other fragments of the antibodies useful in the present invention may be used for the detection and quantitation of the MORT-1 protein according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the MORT-1 in a sample or to detect presence of cells which express the MORT-1 of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the MORT-1 of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the MORT-1, but also its distribution on the examined tissue. Using the present invention, those of ordinary skill will readily perceive that any of wide variety of histological methods (such as staining procedures) can be modified in order to achieve such in situ detection.

Such assays for the MORT-1 of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capably of identifying the MORT-1 protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T, incorporated by reference herein. The radioactive isotope can be detected by such means as the use of a y counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and the contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The MORT-1 of the invention may then be produced by any standard recombinant DNA procedure (see for example, Sambrook, et al., 1989) in which suitable eukaryotic or prokaryotic host cells are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins are the derivatives produced by standard modification of the proteins or their analogs or fragments, produced by the transformed hosts.

The present invention also relates to pharmaceutical compositions comprising recombinant animal virus vectors encoding the MORT-1 protein, which vector also encodes a virus surface protein capable of binding specific target cell (e.g., cancer cells) surface proteins to direct the insertion of the MORT-1 sequence into the cells. Other aspects of the invention will be apparent from the following examples.

The invention will now be described in more detail in the following non-limiting examples and the accompanying drawings:

EXAMPLE 1

Cloning and Isolation of the MORT-1 Protein which Binds to the Intracellular Domain of the FAS-R (i) Two-Hybrid Screen and Two-Hybrid β-Galactosidase Expression Test To isolate proteins interacting with the intracellular domain of the FAS-R, the yeast two-hybrid system was used (Fields and Song, 1989; see also co-pending IL 109632, 112002 and 112692). Briefly, this two-hybrid system is a yeast-based genetic assay to detect specific protein-protein interactions in vivo by restoration of a eukaryotic transcriptional activator such as GAL4 that has two separate domains, a DNA binding and an activation domain, which domains when expressed and bound together to form a restored GAL4 protein, is capable of binding to an upstream activating sequence which in turn activates a promoter that controls the expression of a reporter gene, such as lacZ or HIS3, the expression of which is readily observed in the cultured cells. In this system the genes for the candidate interacting proteins are cloned into separate expression vectors. In one expression vector the sequence of the one candidate protein is cloned in phase with the sequence of the GAL4 DNA-binding domain to generate a hybrid protein with the GAL4 DNA-binding domain, and in the other vector the sequence of the second candidate protein is cloned in phase with the sequence of the GAL4 activation domain to generate a hybrid protein with the GAL4-activation domain. The two hybrid vectors are then co-transformed into a yeast host strain having a lacZ or HIS3 reporter gene under the control of upstream GAL4 binding sites. Only those transformed host cells (co-transformants) in which the two hybrid proteins are expressed and are capable of interacting with each other, will be capable of expression of the reporter gene. In the case of the lacZ reporter gene, host cells expressing this gene will become blue in color when X-gal is added to the cultures. Hence, blue colonies are indicative of the fact that the two cloned candidate proteins are capable of interacting with each other.

Using this two-hybrid system, the intracellular domain, FAS-IC, was cloned, separately, into the vector pGBT9 (carrying the GAL4 DNA-binding sequence, provided by Clontech, USA, see below), to create fusion proteins with the GAL4 DNA-binding domain. For the cloning of FAS-R into pGBT9, a clone encoding the full-length cDNA sequence of FAS-R (see co-pending IL 111125) was used from which the intracellular domain (IC) was excised by standard procedures using various restriction enzymes and then isolated by standard procedures and inserted into the pGBT9 vector opened, in its multiple cloning site region (MCS), with the corresponding suitable restriction enzymes. It should be noted that the FAS-IC extends from residues 175-319 of the intact FAS-R, this portion containing residues 175-319 being the FAS-IC inserted into the pGBT9 vector (see also IL 111125).

The above hybrid (chimeric) vector was then co-transfected together with a cDNA library from human HeLa cells cloned into the pGAD GH vector, bearing the GAL4 activating domain, into the HF7c yeast host strain (all the above-noted vectors, pGBT9 and pGAD GH carrying the HeLa cell cDNA library, and the yeast strain were purchased from Clontech Laboratories, Inc., USA, as a part of MATCHMAKER Two-Hybrid System, #PT1265-1). The co-transfected yeasts were selected for their ability to grow in medium lacking Histidine (His-medium), growing colonies being indicative of positive transformants. The selected yeast clones were then tested for their ability to express the lacZ gene, i.e., for their LAC Z activity, and this by adding X-gal to the culture medium, which is catabolized to form a blue colored product by β-galactosidase, the enzyme encoded by the lacZ gene. Thus, blue colonies are indicative of an active lacZ gene. For activity of the lacZ gene, it is necessary that the GAL4 transcription activator be present in an active form in the transformed clones, namely that the GAL4 DNA-binding domain encoded by the above hybrid vector be combined properly with the GAL4 activation domain encoded by the other hybrid vector. Such a combination is only possible if the two proteins fused to each of the GAL4 domains are capable of stably interacting (binding) to each other. Thus, the His$^+$ and blue (LAC Z$^+$) colonies that were isolated are colonies which have been co-transfected with a vector encoding FAS-IC and a vector encoding a protein product of human HeLa cell origin that is capable of binding stably to FAS-IC.

The plasmid DNA from the above His$^+$, LAC Z$^+$ yeast colonies was isolated and electroporated into *E. coli* strain HB101 by standard procedures followed by selection of Leu$^+$ and Ampicillin resistant transformants, these transformants being the ones carrying the hybrid pGAD GH vector which has both the Amp$^R$ and Leu$^2$ coding sequences. Such transformants therefore are clones carrying the sequences encoding newly identified proteins capable of binding to the FAS-IC. Plasmid DNA was then isolated from these transformed *E. coli* and retested by:

(a) retransforming them with the original FAS-R intracellular domain hybrid plasmid (hybrid pGTB9 carrying the FAS-IC) into yeast strain HF7 as set forth hereinabove. As controls, vectors carrying irrelevant protein encoding sequences, e.g., pACT-lamin or pGBT9 alone were used for co-transformation with the FAS-IC-binding protein (i.e., MORT-1)encoding plasmid. The co-transformed yeasts were then tested for growth on His$^-$ medium alone, or with different levels of 3-aminotriazole; and (b) retransforming the plasmid DNA and original FAS-IC hybrid plasmid and control plasmids described in (a) into yeast host cells of strain SFY526 and determining the LAC Z⁺ activity (effectivity of β-gal formation, i.e., blue color formation).

The results of the above tests revealed that the pattern of growth of colonies in His⁻ medium was identical to the pattern of LAC Z activity, as assessed by the color of the colony, i.e., His colonies were also LAC Z⁺. Further, the LAC Z activity in liquid culture (preferred culture conditions) was assessed after transfection of the GAL4 DNA-binding and activation-domain hybrids into the SFY526 yeast hosts which have a better LAC Z inducibility with the GAL4 transcription activator than that of the HF-7 yeast host cells.

Using the above procedure a protein called HF1, and now also called MORT-1 for "Mediator of Receptor-induced Toxicity", was identified, isolated and characterized.

Furthermore, it should also be mentioned that in a number of the above two-hybrid, β-galactosidase expression tests, the expression of β-galactosidase was also assessed by a preferred filter assay. In the screening, 5 of about 3×10⁶ cDNAs were found to contain the MORT-1 insert. The so-isolated cloned MORT-1 cDNA inserts were then sequenced using standard DNA sequencing procedures. The amino acid sequence of MORT-1 was deduced from the DNA sequence. Residue numbering in the proteins encoded by the cDNA inserts are as in the Swiss-Prot data bank. Deletion mutants were produced by PCR, and point mutants by oligonucleotide-directed mutagenesis (Current Protocols in Molec. Biol., 1994).

(ii) Induced Expression, Metabolic Labeling and Immunoprecipitation of Proteins

MORT-1, N-linked to the FLAG octopeptide (FLAG-HF1; Eastman Kodak, New Haven, Conn., USA), Fas-IC, FAS-R, p55-R' a chimera comprised of the extracellular domain of p55-R (amino acids 1-168) fused to the transmembrane and intracellular domain of FAS-R (amino acids 153-319), and the luciferase cDNA which serves as a control, were expressed in HeLa cells. Expression was carried out using a tetracycline-controlled expression vector, in a HeLa cell clone (HtTA-I) that expresses a tetracycline-controlled transactivator (Gossen and Bujard, 1992; as described in PCT/US95/05854; see also Boldin et al., 1995). Metabolic labeling with [³⁵S]methionine and [³⁵S]cysteine (DuPont, Wilmington, Del., USA and Arnersham, Buckinghamshire, England) was performed 18 hours after transfection, by a further 4-hour incubation at 37° C. in Dulbecco's modified Eagle's medium lacking methionine and cysteine, but supplemented with 2% dialyzed fetal calf serum. The cells were then lysed in RIPA buffer (10 mM Tris-HCl, pH 7.5, 150 mM NaCl, 1% NP-40, 1% deoxycholate, 0.1% SDS and 1 mM EDTA) and the lysate was pre-cleared by incubation with irrelevant rabbit antiserum (3 μl/ml) and Protein G Sepharose beads (Pharmacia, Uppsala, Sweden; 60 μl/ml). Immunoprecipitation was performed by 1-hour incubation at 4° C. of 0.3 ml aliquots of lysate with mouse monoclonal antibodies (5 μl/aliquot) against the FLAG octopeptide (M2; Eastman Kodak), p55-R (#18 and #20; (Engelmann et al., 1990)), or FAS-R (ZB4; Kamiya Southand Oaks, Calif., USA), or with isotype matched mouse antibodies as a control, followed by a further 1-hour incubation with Protein G Sepharose beads (30 μl/aliquot).

(iii) In Vitro Binding

Glutathione S-transferase (GST) fusions with the wild type or a mutated FAS-IC were produced and adsorbed to glutathione-agarose beads (as described in L 109632, 111125, 112002, 112692; see also Boldin et al., 1995; Current Protocols in Molecular Biology, 1994; Frangioni and Neel, 1993). Binding of metabolically-labeled FLAG-HF1 fusion protein to GST-Fas-IC was assessed by incubating the beads for 2 hours at 4° C. with extracts of HeLa cells, metabolically labeled with [³⁵S]methionine (60 μCi/ml), that express FLAG-HF1. The extracts were prepared in a buffer containing 50 mM Tris-HCl, pH 7.5, 150 mM NaCl, 0.1% NP-40, 1 mM dithiotreitol, 1 mM EDTA, 1 mM phenylmethylsulfonyl fluoride, 20 μg/ml Aprotonin, 20 μg/ml Leupeptin, 10 mM sodium fluoride and 0.1 mM sodium vanadate (1 ml per 5×10⁵ cells).

(iv) Assessment of the Cytotoxicity Triggered by Induced Expression of HF1

HF1, Fas-IC, p55-IC and luciferase cDNAs were inserted into a tetracycline-controlled expression vector and transfected to HtTA-1 cells (a HeLa cell line) (Gossen and Bujard, 1992) together with the secreted placental alkaline phosphatase cDNA, placed under control of SV40 promoter (the pSBC-2 vector (Dirks et al., 1993)). Cell death was assessed 40 hours after transfection, either by the neutral-red uptake assay (Wallach, 1984) or, for assessing specifically the death in those cells that express the transfected cDNAs, by determining the amounts of placental alkaline phosphatase (Berger et al., 1988) secreted to the growth medium at the last 5 hours of incubation.

In another set of experiments to analyze the region of the MORT-1 (HF1) protein involved in the binding to the FAS-IC, the following proteins were expressed transiently in HeLa cells that contain a tetracycline-controlled transactivator (HtTA-l), using a tetracycline-controlled expression vector (pUHD10-3): Human FAS-R alone; Human FAS-R as well as the N-terminal part of MORT-1 (amino acids 1-117, the "MORT-1 head"); Human FAS-R as well as the C-terminal part of MORT-1, which contains its 'death domain' homology region (amino acids 130-245, the "MORT-1 DD", see also L 112742); FLAG-55.11 (amino acids 309-900 of protein 55.11 fused at the N-terminus to the FLAG octapeptide, the protein 55.11 being a p55-IC-specific binding protein, see also L 109632). Twelve hours after transfection, the cells were trypsinized and re-seeded at a concentration of 30,000 cells/well. After 24 hours further incubation, the cells were treated for 6 hours with a monoclonal antibody against the extracellular domain of FAS-R (monoclonal antibody CH-11, Oncor) at various concentrations (0.001-10 μg/ml monoclonal antibody), in the presence of 10 g/ml cycloheximide. Cell viability was then determined by the neutral-red uptake assay and the results were presented in terms of % viable cells as compared to cells that had been incubated with cycloheximide alone (in the absence of anti-FAS-R monoclonal antibody CH11).

(v) Northern and Sequence Analyses poly A⁺ RNA was isolated from total RNA of HeLa cells (Oligotex-dT mRNA kit. QIAGEN, Hilden, Germany). Northern analysis using the HF1 cDNA as a probe was performed by conventional methods (as described in PCT/US95105854; see also Boldin et al., 1995). The nucleotide sequence of MORT-1 (HF1) was determined in both directions by the dideoxy chain termination method.

The results (shown in Table 1 and FIGS. 1-7) obtained from the above experimental procedures are as follows: Sequence analysis of the MORT-1 cDNA cloned by the two-hybrid procedure indicated that it encodes a novel protein (see below). Applying the two-hybrid test further to evaluate the specificity of the binding of this protein (MORT-1) for "Mediator of Receptor-induced Toxicity") to FAS-IC, and to define the particular region in FAS-IC to which it binds, led to the following findings (Table 1): (a) The protein binds both to human and to mouse FAS-IC, but not to several other tested proteins, including three receptors of the TNF/NGF receptor family (p55 and p75 TNF receptors and CD40); (b) Replacement mutations at position 225 (Ile) in the 'death domain' of FAS-R, shown to abolish signaling both in vitro and in vivo (the lpr$^{cg}$ mutation (Watanabe-Fukunaga et al., 1992; Itoh and Nagata, 1993), also prevents binding of MORT-1 to the FAS-IC; (c) The MORT-1 binding-site in FAS-R occurs within the 'death domain' of this receptor; and (d) MORT-1 binds to itself. This self-binding, and the binding of HF1 to FAS-R involve different regions of the protein: A fragment of MORT-1 corresponding to residues 1-117 binds to the full-length MORT-1, but does not bind to itself nor to the FAS-IC. Conversely, a fragment corresponding to residues 130-245 binds to FAS-R, yet does not bind to MORT-1 (Table 1). Furthermore, it is apparent from the results in Table 1 that the 'death domain' region of FAS-R is critical for FAS-IC self-association, as is the 'death domain' region of p55-R for p55-IC self-association. The deletions on both sides of these 'death domains' does not affect the self-association ability thereof while, however, a deletion within these 'death domains' does affect the self-association. In the case of MORT-1, the binding of MORT-1 to FAS-IC is also dependent upon the complete (full) 'death domain' of FAS-R, while however, it is also not dependent on the regions outside of the FAS-R 'death domain' region for FAS-IC binding.

TABLE 1

Interaction of MORT-1 with FAS-IC and Self-Association of MORT-1 within Transformed Yeasts: Assessment by a Two-Hybrid β-Galactose Expression Test

| DNA-BINDING-DOMAIN HYBRID | ACTIVATION-DOMAIN HYBRID | | | | | |
|---|---|---|---|---|---|---|
| | MORT1 | | | human | | |
| | Full | 1-117 | 130-245 | Fas-IC | SNF4 | pGAD-GH |
| Human Fas-IC | | | | | | |
| Full (175, 200, 210, 233, 304, 319) 'Death Domain' | ++ | − | + | ++ | − | − |
| 200–319 | ++ | | | ++ | − | − |
| 233–319 | − | | | − | − | − |
| 175–304 | ++ | − | + | ++ | − | − |
| Mouse Fas-IC | | | | | | |
| Full (166, 197, 292, 306) | ++ | − | ++ | ++ | − | − |
| 197–306 | ++ | − | + | ++ | − | − |
| I225N N$^{2.86}$ | − | − | − | ++ | − | − |
| I225A A$^{2.38}$ | − | | | ++ | − | − |
| MORT1 | | | | | | |
| Full (117, 130, 153, 215, 245) 'Death Domain motif' | ++ | ++ | − | ++ | − | − |
| 1–117 | + | − | | − | − | − |
| 130–245 | − | − | ++ | − | − | |

SPECIFICITY TESTS

TABLE 1-continued

Interaction of MORT-1 with FAS-IC and Self-Association of
MORT-1 within Transformed Yeasts: Assessment by a Two-Hybrid
β-Galactose Expression Test

| DNA-BINDING-DOMAIN HYBRID | ACTIVATION-DOMAIN HYBRID | | | | | |
|---|---|---|---|---|---|---|
| | MORT1 | | | human | | |
| | Full | 1-117 | 130-245 | Fas-IC | SNF4 | pGAD-GH |
| human p55-IC | − | | | − | − | − |
| human p75-IC | − | | | − | − | − |
| human CD40-IC | − | | | − | − | − |
| Cyclin D | − | | | − | − | − |
| Lamin | − | | | − | − | − |
| SNF1 | − | | | − | + | − |
| pGBT9 | − | | | − | − | − |

In Table 1 above there is depicted the interaction of the proteins encoded by the Gal4 DNA binding domain and activation-domain constructs (pGBT9 and pGAD-GH) within transfected SFY526 yeasts as assessed by β-galactosidase expression filter assay. The DNA-binding-domain constructs included four constructs of the human FAS-IC, four constructs of the mouse FAS-IC including two full-length constructs having Ile to Leu or Ile to Ala replacement mutations at position 225 (I225N and I225A, respectively), and three HF1 (MORT-1) constructs, all of which constructs are shown schematically on the left-hand side of the table. The activation-domain constructs included three HF1 constructs, the HF1 portion being as in the DNA-binding-domain constructs; and a full-length human FAS-IC construct, the FAS-IC portion being the same as in the above DNA-binding domain construct. The intracellular domains of human p55 TNF receptor (p55-IC residues 206-426), human CD40 (CD40-IC, residues 216-277) and human p75 TNF receptor (p75-IC, residues 287-461) as well as lamin, cyclin D and 'empty' Gal4 (pGBT9) vectors served as negative controls in the form of DNA-binding domain constructs. SNF1 and SNF4 served as positive controls in the form of DNA-binding-domain (SNF1) and activation-domain (SNF4) constructs. 'Empty' Gal4 vectors (pGAD-GH) also served as negative controls in the form of activation domain constructs (for more details concerning the p55-IC, p75-IC, see also PCT/US95/05854). The symbols "++" and "+" denote the development of strong color within 30 and 90 minutes of the assay, respectively; and "−" denotes no development of color within 24 hours. Combinations for which no score is given have not been tested.

Expression of HF1 (MORT-1) molecules fused at their N terminus with the FLAG octapeptide (FLAG-HF1) yielded in HeLa cells proteins of four distinct sizes—about 27, 28, 32, and 34 kD. In FIGS. 1(A and B) there is shown the results demonstrating the interaction of HF1 with FAS-IC in vitro. As noted above in the description of FIGS. 1A and B, FIG. 1A is a reproduction of a control autoradiogram of an immunoprecipitate of proteins from extracts of HeLa cells transfected with the FLAG-HF1 (FLAG-MORT1) fusion protein or with luciferase cDNA as a control, the immunoprecipitation being performed with anti-FLAG antibody (αFLAG). FIG. 1B is a reproduction of an autoradiogram showing the interaction in vitro between HF1 and FAS-IC wherein the HF1 is in the form of [$^{35}$S]methionine-metabolically labeled HF1-FLAG fusion proteins obtained from extracted of transfected HeLa cells and the FAS-IC is in the form of human and mouse GST-FAS-IC fusion proteins including one having a replacement mutation at position 225 in FAS-IC, all of which GST-FAS-IC fusion proteins were produced in E. coli. The GST-fusion proteins were attached to glutathione beads before interaction with the extracts containing the HF1-FLAG fusion protein following this interaction, SDS-PAGE was performed. Thus the in vitro interaction was evaluated by assessing, by autoradiography following SDS-PAGE, the binding of [$^{35}$S] metabolically labeled HF1, produced in transfected HeLa cells as a fusion with the FLAG octapeptide (FLAG-HF1), to GST, GST fusion with the human or mouse FAS-IC (GST-huFAS-IC, GST-mFAS-IC) or to GST fusion with FAS-IC containing an Ile to Ala replacement mutation at position 225. As is apparent from FIG. 1B, all four FLAG-HF1 proteins showed ability to bind to FAS-IC upon incubation with a GST-FAS-IC fusion protein. As in the yeast two-hybrid test (Table 1), HF1 did not bind to a GST-FAS-IC fusion protein with a replacement at the lpr$^{cg}$ mutation site (I225A).

The proteins encoded by the FLAG-HF1 cDNA showed also an ability to bind to the intracellular domain of FAS-R, as well as to the intracellular domain of FAS-R chimera whose extracellular domain was replaced with that of p55-R (p55-FAS), when co-expressed with these receptors in HeLa cells. In FIGS. 2(A, B, C) there is shown the results demonstrating the interaction of HF1 with FAS-IC in transfected HeLa cells, i.e., in vivo. As mentioned above in the description of FIGS. 2 A, B, C, these figures are reproductions of autoradiograms of immunoprecipitates of various transfected HeLa cells which demonstrate the in vivo interaction and specificity of the interaction between HF1 and FAS-IC in cells co-transfected with constructs encoding these proteins. Thus, FLAG-HF1 fusion protein was expressed and metabolically labeled with [$^{35}$S]cysteine (20 μCi/ml) and [$^{35}$S]methionine (40 μCi/ml) in HeLa cells, alone, or together with human FAS-R, FAS-R chimera in which the extracellular domain of FAS-R was replaced with the corresponding region in the human p55-R (p55-FAS), or the human p55-R, as negative control. Cross-immunoprecipitation of HF1 with the co-expressed receptor was performed using the indicated antibodies (FIGS. 2AC). As is apparent in FIGS. 2A-C, FLAG-HF1 is capable of binding to the intracellular domain of FAS-R, as well as to the intracellular domain of a FAS-R-p55-R chimera having the extracellular domain of p55-R and the intracellular domain of FAS-R, when co-expressed with these receptors in the HeLa cells (see 3 middle lanes FIG. 2A and 3 left-hand lanes FIG. 2C, respectively). Further, immunoprecipitation of FLAG-HF1 from extracts of the transfected cells also resulted in precipitation of the co-expressed FAS-R (FIG. 2A) or the co-expressed p55-FAS chimera (FIG. 2C). Conversely, immunoprecipitation of these receptors resulted in the co-precipitation of the FLAG-HF1 (FIGS. 2A and 2C).

Northern analysis using the HF1 cDNA as probe revealed a single hybridizing transcript in HeLa cells. FIG. 3 is shows a reproduction of a Northern blot in which poly A+ RNA (0.3 µg) from transfected cells was hybridized with the HF1 cDNA. The size of this transcript (about 1.8 kB) is close to that of the HF1 cDNA (about 1702 nucleotides).

In sequence analysis, the cDNA was found to contain an open reading frame of about 250 amino acids. FIG. 4 depicts the preliminary nucleotide and deduced amino acid sequence of HF1 in which the 'death domain' motif is underlined, as is a possible start Met residue (position 49; bold, underlined M) and the translation stop codon (the asterisk under the codon at position 769-771). This 'death domain' motif shares homology with the known p55R and FAS-R 'death domain' motifs (p55-DD and FAS-DD). In order to determine the precise C-terminal end of HF1 and to obtain evidence concerning the precise N-terminal (initial Met residue) end of HF1, additional experiments were carried out as follows:

Using the methods described above, a number of constructs encoding HF1 molecules fused at their N-terminus with the FLAG octapeptide (FLAG-HF1) were constructed and expressed in HeLa cells with metabolic labeling of the expressed proteins using 35S-cysteine and $^3$S -methionine (see the above in respect of FIG. 5B). The HF1-FIAG molecules were encoded by the following cDNAs containing different portions of the HF1-encoding sequence:

(i) The FLAG octapeptide cDNA linked to the 5' end of the HF1 cDNA from which nucleotides 1-145 (see FIG. 4) have been deleted;

(ii) The FLAG octapeptide cDNA linked to the 5' end of the HF1 full-length cDNA (see FLAG-HF1 construct above in respect of FIG. 1B);

(iii) The FLAG octapeptide cDNA linked to the 5' end of the HF1 cDNA from which nucleotides 1-145 as well as nucleotides 832-1701 (see FIG. 4) had been deleted and the codon GCC at position 142-144 was mutated to TCC to prevent start of translation at this site.

Figure 5:
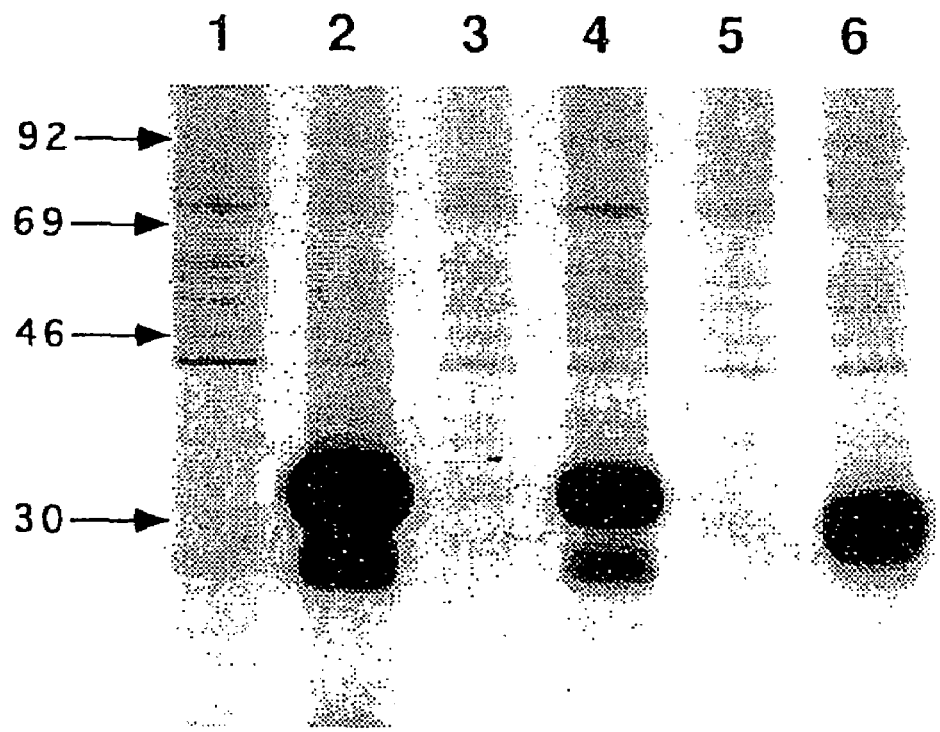

Following expression of the above HF1-FLAG fusion products, immunoprecipitation was carried out as mentioned above, using either anti-FLAG monoclonal antibodies (M2) or as a control, anti-p75 TNF-R antibodies (#9), followed by SDS-PAGE (10% acrylamide) and autoradiography. The results are shown in FIG. 5 which is a reproduction of an autoradiogram on which was separated the above noted HF1-FLAG fusion proteins, the samples loaded on each lane of the gel being as follows:

Lanes 1 and 2: HF1-FLAG fusion protein encoded by the FLAG octapeptide cDNA linked to the 5' end of the HF1 cDNA from which nucleotides 1-145 had been deleted.

Lanes 3 and 4: HF1-FLAG fusion protein encoded by the FLAG octapeptide cDNA linked to the 5' end of the full length HF1 cDNA.

Lanes 5 and 6: HF-1-FLAG fusion protein encoded by the FLAG octapeptide cDNA linked to the 5' end of the HF1 cDNA from which nucleotides 1-145 as well as 832-1701 had been deleted and the GCC at position 142-144 was mutated to TCC to prevent start of translation at this site.

The immunoprecipitations were with anti-FLAG monoclonal antibodies for the samples in lanes 2, 4 and 6 and anti-p75 TNF-R antibodies for the samples in lanes 1, 3 and 5.

From the autoradiogram of FIG. 5 it is apparent that the identity of product sizes in lanes 2 and 4 confirms that the nucleotides 769-771 are the site of translation termination for HF1, i.e., this codon represents a stop signal and is indicated by an asterisk in FIG. 4. Further, the occurrence of a broad band which represents just two translation products (as seen on the gel but being strongly labeled becomes a single large band on the autoradiogram) in lane 6 indicates that the occurrence of two additional products (the higher molecular weight broad bands) in lanes 2 and 4 reflect the initiation of translation both at the N-terminus of the FLAG-HF1 fusion molecule and at the methionine residue number 49 within the HF1 sequence (see bold underlined M at position 49 of the amino acid sequence in FIG. 4). Thus, the above results have confirmed (validated) the C-terminal end of HF1 and have provided evidence that the N-terminal end of HF 1 may be at position 49 of the sequence in FIG. 4.

Indeed, it has been shown by additional expression experiments of HF1 without the FLAG octapeptide fused to its 5-end, that Met$^{49}$ serves as an effective site of translation initiation.

It should be mentioned that a search conducted in the 'Gene Bank' and Protein Bank' DataBases revealed that there is no sequence corresponding to that of HF1 depicted in FIG. 4. Thus, HF1 represents a new FAS-IC-specific binding protein.

Figure 6A:
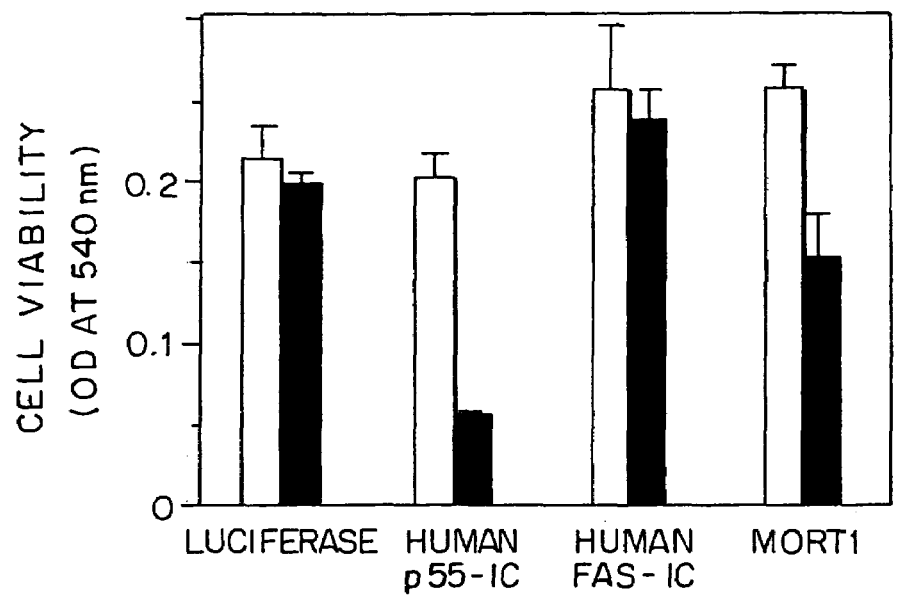
FIGS. 6A and B are also described in Example 1.
Figure 6B:
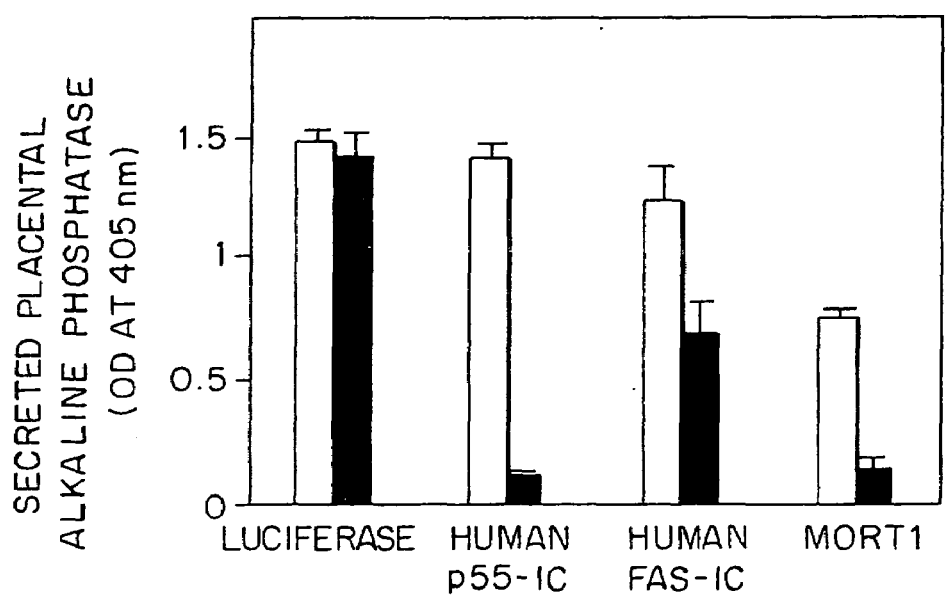
FIGS. 6(A and B) depict graphically the ligand-independent triggering of cytocidal effects in cells transfected with MORT-1, wherein cell viability was determined either by the neutral red uptake assay (FIG. 6A), or for specifically determining the viability of cells that expressed the transfected DNA, by measuring the amounts of placental alkaline phosphatase secreted into the medium (FIG. 6B). HeLa cells were transfected with tetracycline-controlled expression vectors encoding HF1 (MORT1), human FAS-IC, human p55-IC, or luciferase (control), and in all cases also with a cDNA encoding the secreted alkaline phosphatase, which permitted the evaluation of the effect of transient expression of these proteins on the viability of the cells. In both FIGS. 6A and 6B the open graphs represent transfected cells grown in the presence of tetracycline (1 μg/ml, to block expression) and the closed graphs represent transfected cells grown in the absence of tetracycline.

High expression of p55-IC results in triggering of a cytocidal effect (see L 109632, 111125 and Boldin et al., 1995). The expression of FAS-IC in HeLa cells also has such an effect, though to a lower extent, which could be detected only with the use of a sensitive assay. In FIGS. 6A and B there is depicted graphically the ligand independent triggering of cytocidal effects in cells transfected with HF1, as well as human p55-IC and FAS-IC. The effect of transient expression of HF1, human FAS-IC, human p55-IC, or luciferase that served as a control, on the viability of HeLa cells was assessed using a tetracycline-controlled expression vector. Cell viability was evaluated 40 minutes after transfecting these cDNAs either in presence (open bars, FIGS. 6A and B) or absence (closed bars, FIGS. 6A and B) of tetracycline (1 µg/ml, to block expression), together with a cDNA encoding the secreted placental alkaline phosphatase. Cell viability was determined either by the neutral red uptake assay (FIG. 6A) or, for determining specifically the viability of those particular cells that express the transfected DNA, by measuring the amounts of placental alkaline phosphatase secreted to the growth medium (FIG. 6B).

Thus, it is apparent from FIGS. 6A and B that the expression of HF1 in HeLa cells resulted in significant cell death, greater than that caused by FAS-IC expression. These cytotoxic effects of all of p55-IC, FAS-IC and HF1 seem to be related to the 'death domain' regions, present in all of these proteins, which 'death domains' have a propensity to self-associate, and thereby possibly prompting the cytotoxic effects.

In view of the above mentioned characteristics of HF1 (MORT-1), namely, the specific association of HF1 with that particular region in FAS-R which is involved in cell death induction, and the fact that even a slight change of structure in that region, which prevents signaling (the lpr$^{cg}$ mutation) abolishes also the binding of HF1, indicates that this protein plays a role in the signaling or triggering of cell death. This notion is further supported by the observed ability of HF1 to trigger by itself a cytocidal effect. Thus, HF1 (MORT-1) may function as (i) a modulator of the self-association of FAS-R by its own ability to bind to FAS-R as well as to itself, or (ii) serve as a docking site for additional proteins that are involved in the FAS-R signaling, i.e., HF1 may be a 'docking' protein and may therefore bind other receptors besides FAS-R, or (iii) constitutes part of a distinct signaling system that interacts with FAS-R signaling.

In order to further analyze the regions of MORT-1 (HF1) involved in FAS-IC binding and modulation of the FAS-R-mediated cellular effects (cytotoxicity), the abovementioned experiments were carried out, using vectors encoding portions of MORT-1 (the 'MORT-1 head', amino acids 10117 and the 'MORT-1 dd', amino acids 130-245) (separately), with a vector encoding the human FAS-R for co-transfections of HeLa cells. In these experiments the various proteins and combinations of proteins were expressed transiently in HeLa cells that contain a tetracycline-controlled transactivator (HtTA-1) by inserting the sequences encoding the proteins into a tetracycline-controlled expression vector PUHD10-3. Control transfections employed vectors encoding only the FAS-R and vectors encoding the FLAG-55.11 fusion protein (the 55.11 protein being a p55-IC-specific binding protein of which a portion containing amino acids 309-900 was fused (at its N-terminal) to the FLAG octapeptide).

Following the transfection and incubation periods (see (iv) above) the transfected cells were treated with various concentrations of an anti-FAS-R monoclonal antibody (CH-11) which binds specifically to the extracellular domain of FAS-R expressed by cells. This binding of anti-FAS-R antibody induces the aggregation of the FAS-R at the cell surface (much like the FAS-R ligand) and induces the intracellular signaling pathway mediated by the FAS-IC, resulting, ultimately, in cell death (FAS-R mediated cell cytotoxicity). The concentrations of the anti-FAS-R monoclonal antibody (CH11) used were in the range of 0.01-10 µg/ml, usually concentrations such as 0.005; 0.05; 0.5 and 5 µg/ml. The cells were treated with the anti-FAS antibody in the presence of 10 µg/ml cycloheximide.

Figure 7:
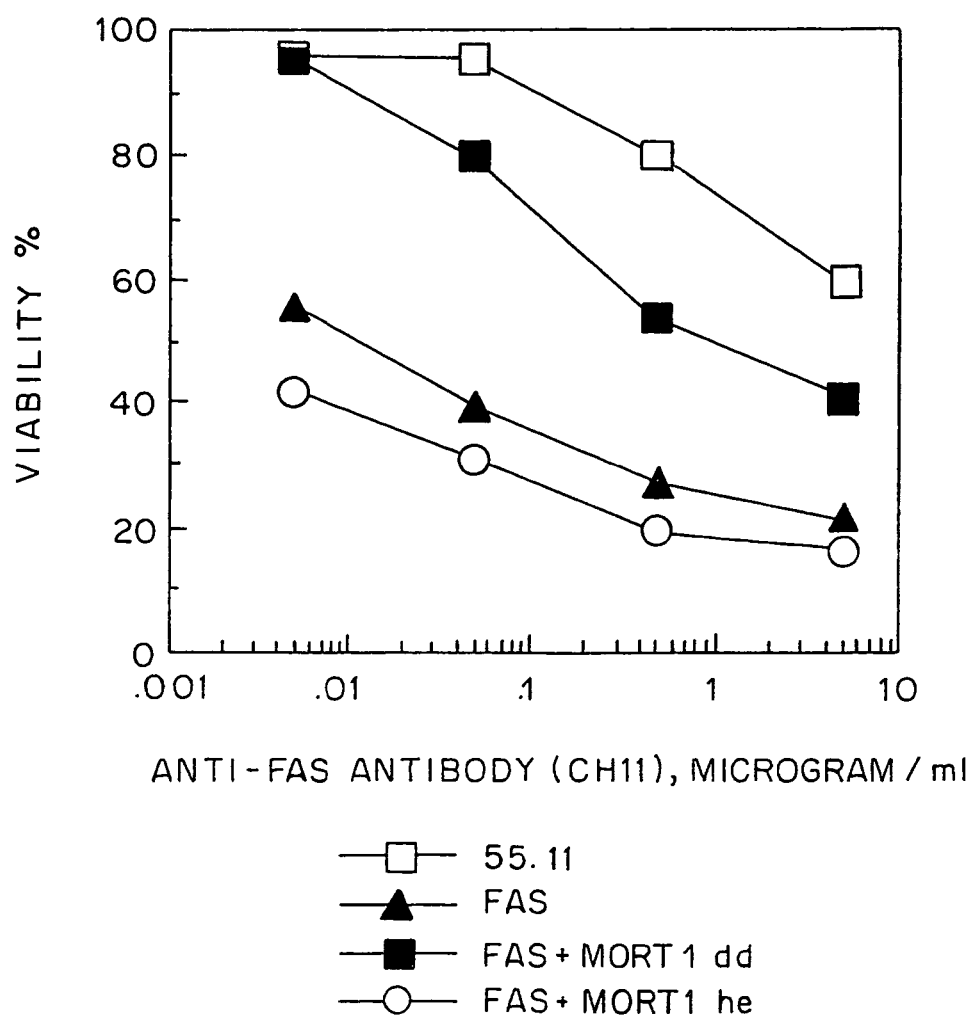
FIG. 7 is a graphic representation of the effects of different portions of the MORT-1 protein on the cell cytotoxic effects mediated by FAS-R, as described in Example 1.

The results of the above analysis are set forth graphically in FIG. 7 which depicts the % viability of the transfected cells as a function of the concentration of anti-FAS-R monoclonal antibody (CH11) used to treated the ceils, for each of the four different groups of transfected cells. These groups of transfected cells are denoted by different symbols as follows: (i) the open squared denote cells transfected only with the non-relevant (i.e., non-FAS-IC binding) control vector encoding the FLAG-55.11 fusion protein ("55.11", negative control); (ii) the closed squared denote cells co-transfected with vectors encoding the FAS-R and vectors encoding the C-terminal portion of MORT-1, amino acids 130-245, which contains the MORT-1 'death domain' (dd) homology region ("fas+mortldd"); (iii) the closed triangles denote cells transfected with only the vector encoding the FAS-R ("fas", positive control); and (iv) the open circles denote cells co-transfected with vectors encoding the FAS-R and vectors encoding the N-terminal portion of MORT-1, amino acids 1-117, the 'MORT1 head' ("fas+mortlhe").

From the results presented in FIG. 7, it is apparent that the expression of FAS-R in the transfected cells conveys an increased sensitivity to the cytocidal effects of the anti-FASR antibodies (compare "fas" to "55.11"). Further, the co-expression of the region in MORT1 that contains the 'death domain' homology region and FAS-R ("fas+mortldd") strongly interferes with FAS-induced (i.e., FAS-R mediated) cell death as would be expected from the ability (see Table 1 above) of the MORT-1 'death domain' (DD) region to bind to the FAS-R 'death domain' (FAS-DD). Moreover, co-expression of the N-terminal part of MORT-1 and FAS-R ("fas+mortlhe") does not interfere with FAS-R-mediated cell death and, if at all, somewhat enhances the cytotoxicity (i.e., slightly increased cell death)

Thus, the above results clearly indicate that the MORT-1 protein has two distinct regions as far as binding to the FAS-IC and mediation of the cell-cytotoxic activity of the FAS-IC are concerned.

These results therefore also provide a basis for the use of different parts (i.e., active fragments or analogs) of the MORT-1 protein for different pharmaceutical applications. For example, the analogs or fragments or derivatives thereof of the MORT-1 protein which contain essentially only the C-terminal portion of MORT-1 inclusive of its 'death domain' region may be used for inhibiting FAS-R-mediated cytotoxic effects in FAS-R containing cells or tissues and thereby protect these cells or tissues from the deleterious effects of the FAS-R ligand in cases such as, for example, acute hepatitis. Alternatively, the analogs or fragments or derivatives thereof of the MORT-1 protein which contain essentially only the N-terminal portion of MORT-1 may be used for enhancing the FAS-R-mediated cytotoxic effects in FAS-R containing cells and tissues, thereby leading to the enhanced destruction of these cells or tissues when desired in cases such as, for example, tumor cells and autoreactive T and B cells. As detailed herein above, the above uses of the different regions of MORT-1 may be carried out using the various recombinant viruses (e.g., Vaccinia) to insert the MORT-1 region-encoding sequence into specific cells or tissues it is desired to treat.

Furthermore, it is also possible to prepare and use various other molecules such as, antibodies, peptides and organic molecules which have sequences or molecular structures corresponding to the above noted MORT-1 regions in order to achieve the same desired effects mediated by these MORT-1 regions.

REFERENCES

Baringa, M. (1993) Science 2621512-4.
Berger, J., Hauber, J., Hauber, R., Geiger, R. and Cullen, B. R. (1988) Gene 66, 1-10.
Beutler, B. and Cerami, C. (1987) NEJM, 316:379 385.
Boldin, M. P. et al. (1995) J. Biol. Chem. 270, 337-341.
Brakebusch, C. et al. (1992) EMBO J., 11 :943-950.
Brockhaus, M. et al. (1990) Proc. Natl. Acad. Sci. USA, 87:3127-3131.
Cantor, G. H. et al. (1993) Proc. Natl. Acad. Sci. USA 90:10932-6.
Chen, C. J. et al. (1992) Ann N.Y. Acad. Sci. 660:271-3.
Crisell, P. et al., (1993) Nucleic Acids Res. (England) 21 (22):5251-5.
Current protocols in molecular biology (Ausubel, F. M., Brent, R., Kingston, R. E., Moore, D. D., Seidman, J. G., Smith, J. A., Struhl, K., Albright, L. M., Coen, D. M. & Varki, A., eds.), (1994) pp. 8.1.1-8.1.6 and 16.7-16.7.8, Greene Publishing Associates, Inc. and Wiley & Sons, Inc., New York.
Dirks, W., Wirth, M. and Hauser, H. (1993) Gene 128 247-249.
Engelmann, H. et al. (1990) J. Biol. Chem., 265:1531-1536.
Fields, S. and Song, O. (1989) Nature, 340:245-246.
Frangioni, J. V. and Neel, B. G. (1993) Anal. Biochem. 210, 179-187.

Gossen, M. and Boujard, H. (1992) Proc. Natl. Acad. Sci. USA, 89:5547-5551.
Heller; R. A. et al. (1990) Proc. Natl. Acad. Sci. USA, 87:6151-6155.
Hohmann, H.-P. et al. (1989) J. Biol. Chem., 264:14927-14934.
Itoh, N. et al. (1991) Cell 66:233.
Itoh, N. and Nagata, S. (1993) J. Biol. Chem. ~, 10932-7.
Joseph, S. and Burke, J. M. (1993) J. Biol. Chem. 268: 24515-8.
Koizumi, M. et al. (1993) Biol. Pharm. Bull (Japan) 16 (9):879-83.
Loetscher, H. et al. (1990) Cell, 61:351-359.
Nophar, Y. et al. (1990) EMBO J., 9:3269-3278.
Piquet, P. F. t al. (1987) J. Exp. Med., 166:1280-89.
Sambrook et al. (1989) Molecular Cloning: A Laboratory Manual.
Cold Spring Harbor Laboratory Press, Cold spring Harbor, N.Y.
Schall, T. J. et al. (1990) Cell, 61:361-370.
Shimayama, T. et al., (1993) Nucleic Acids Symp. Ser. 29:177-8
Shore, S. K. et al. (1993) Oncogene 8:3183-8.
Smith, C. A. et al. (1990) Science, 248:1019-1023.
Song, H. Y. et al. (1994) J. Biol. Chem. 269, 22492-22495.
Tartaglia, L. A. et al. (1993) Cell, 74:845-853.
Tracey, J. T. et al. (1987) Nature, 330:662-664.
Wallach, D. (1984) J. Immunol. 132 2464-9.
Wallach, D. (1986) in: Interferon 7 (Ion Gresser, ed.), pp. 83-122, Academic Press, London
Wallach, D. et al. (1994) Cytokine, 556.
Watanabe-Fukunaga, R. et al. (1992) Nature, =, 314-317.
Wilks, A. F. et al. (1989) Proc. Natl. Acad. Sci. USA, 86:1603-1607.
Zhao, J. J. and Pick, L. (1993) Nature (England) 365:448-51.

What is claimed is:

1. An isolated antigen-binding molecule comprising an antibody, or an antigen-binding fragment thereof, specific for the MORT-1 protein having the amino acid sequence of SEQ ID NO:2.

2. An antigen-binding molecule in accordance with claim 1, wherein said antigen-binding molecule is a polyclonal antibody, a monoclonal antibody, a chimeric antibody or an antigen-binding fragment thereof.

3. An antigen-binding molecule in accordance with claim 2, wherein said antigen-binding molecule is a monoclonal antibody.

4. An antigen-binding molecule in accordance with claim 2, wherein said antigen-binding molecule is a chimeric antibody.

5. An antigen-binding molecule in accordance with claim 1, which is labeled in a manner to facilitate detection.

6. An antigen-binding molecule in accordance with claim 5, wherein said label is an enzyme, a radioactive label, a fluorescent label, a chemiluminescent label or a bioluminescent label.

7. An antigen-binding molecule in accordance with claim 1, wherein said antigen-binding molecule is an antigen-binding fragment.

8. An antigen-binding molecule in accordance with claim 7, wherein said antigen-binding fragment is a Fab or F(ab')$_2$ fragment.

9. A composition comprising an antigen-binding molecule in accordance with claim 1 and a carrier.

* * * * *